US008586319B2

(12) United States Patent
Schuster et al.

(10) Patent No.: US 8,586,319 B2
(45) Date of Patent: Nov. 19, 2013

(54) RECOMBINANT ACE2 POLYPEPTIDE DIMER

(75) Inventors: Manfred Schuster, Schrick (AT); Hans Loibner, Vienna (AT); Evelyne Janzek-Hawlat, Vienna (AT); Bernhard Peball, Vienna (AT); Stefan Stranner, Vienna (AT); Bettina Wagner, Wiener Neustadt (AT); Robert Weik, Hohe Wand-Stollhof (AT)

(73) Assignee: Apeiron Biologics AG, Vienna (AT)

( * ) Notice: Subject to any disclaimer, the term of this patent is extended or adjusted under 35 U.S.C. 154(b) by 478 days.

(21) Appl. No.: 12/664,641

(22) PCT Filed: Jun. 12, 2008

(86) PCT No.: PCT/AT2008/000211
§ 371 (c)(1),
(2), (4) Date: May 3, 2010

(87) PCT Pub. No.: WO2008/151347
PCT Pub. Date: Dec. 18, 2008

(65) Prior Publication Data
US 2010/0310546 A1    Dec. 9, 2010

(30) Foreign Application Priority Data

Jun. 12, 2007  (AT) .................................. A 913/2007
Apr. 8, 2008   (EP) ..................................... 08450052

(51) Int. Cl.
*A61K 38/48* (2006.01)
(52) U.S. Cl.
USPC .......... 435/7.2; 435/325; 435/212; 424/94.63
(58) Field of Classification Search
None
See application file for complete search history.

(56) References Cited

U.S. PATENT DOCUMENTS

| 6,194,556 B1 * | 2/2001 | Acton et al. ................. 536/23.2 |
| 2005/0147600 A1 | 7/2005 | Acton et al. ................ 424/94.64 |

FOREIGN PATENT DOCUMENTS

| EP | 2 108 695 A1 | 10/2009 |
| WO | WO 04/000367 | 12/2003 |
| WO | WO 2004/023270 | 3/2004 |

OTHER PUBLICATIONS

Petrescu et al. ( Glycobiology, vol. 14, No. 2, pp. 103-114, 2004).*
Kohlstedt et al. (Molec. Pharm, vol. 69, No. 5, 2006, pp. 1725-1732).*
Zhong et al. ( Hypertension, vol. 44, 2004, pp. 907-912).*
Corradi et al., (JMB, 2006, vol. 357, pp. 964-974).*
Beniac et al., "Conformational reorganization of the SARS coronavirus spike following receptor binding: implications for membrane fusion," *PLOS One*, 2(10): E1082, 2007.
Office Communication issued in corresponding European patent application No. 08756821.8, dated May 7, 2012. (English translation included).
"Peptide and protein-based therapeutics," Pioneering New Frontiers, Hotel Del Coronado, San Diego, California, pp. 11, Jan. 7-9, 2008.
Donoghue, "A novel angiotensin-converting enzyme-related carboxypeptidase (ACE2) converts angiotensin I to angiotensin 1-9," *Circ. Res.*, 87:E-19, 2000.
Guy et al., "Membrane-associated zinc peptidase families: comparing ACE and ACE2," *Biochim. Biophys. Acta.*, 1751:2-8, 2005.
Imai et al., "Angiotensin-converting enzyme 2 protects from severe acute lung failure," *Nature*, 436:112-6, 2005.
Kost et al., "New feature of angiotensin-converting enzyme: carbohydrate-recognizing domain," *J. Mol. Recognit.*, 13:360-9, 2000.
Prabakaran et al., "A model of the ACE2 structure and function as a SARS-CoV receptor," *Biochem. Biophys. Res. Commun.*, 314:235-41, 2004.
Tipnis et al., "A human homolog of angiotensin-converting enzyme. Cloning and functional expression as a captopril-insensitive carboxypeptidase," *J. Biol. Chem.*, 275:33238-43, 2000.
Towler et al., "ACE2 X-ray structures reveal a large hinge-bending motion important for inhibitor binding and catalysis," *J. Biol. Chem.*, 279:17996-18007, 2004.
Vickers et al., "Hydrolysis of biological peptides by human angiotensin-converting enzyme-related carboxypeptidase," *J. Biol. Chem.*, 277:14838-14843, 2002.
Vincent et al., "Chloroquine is a potent inhibitor of SARS coronavirus infection and spread," *Virol. J.*, 2:69, 2005.
Warner et al., "Angiotensin-converting enzyme 2 (ACE2), but not ACE, is preferentially localized to the apical surface of polarized kidney cells," *J. Biol. Chem.*, 280:39353-39362, 2005.
Office Communication issued in Columbian Patent Application No. 10-1879, dated Nov. 16, 2012.

* cited by examiner

*Primary Examiner* — Hope Robinson
(74) *Attorney, Agent, or Firm* — Fulbright & Jaworski LLP

(57) ABSTRACT

The present invention relates to recombinant ACE2 polypeptide, where the ACE2 polypeptide is present as a dimer. The dimer is formed specifically from glycosylated monomers and is used for producing pharmaceutical products with an extended half-life.

12 Claims, 20 Drawing Sheets

Figure 1:
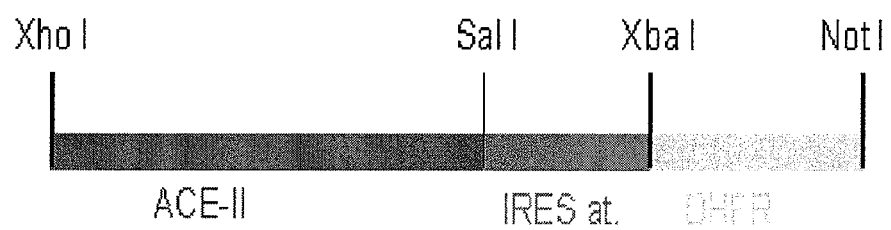

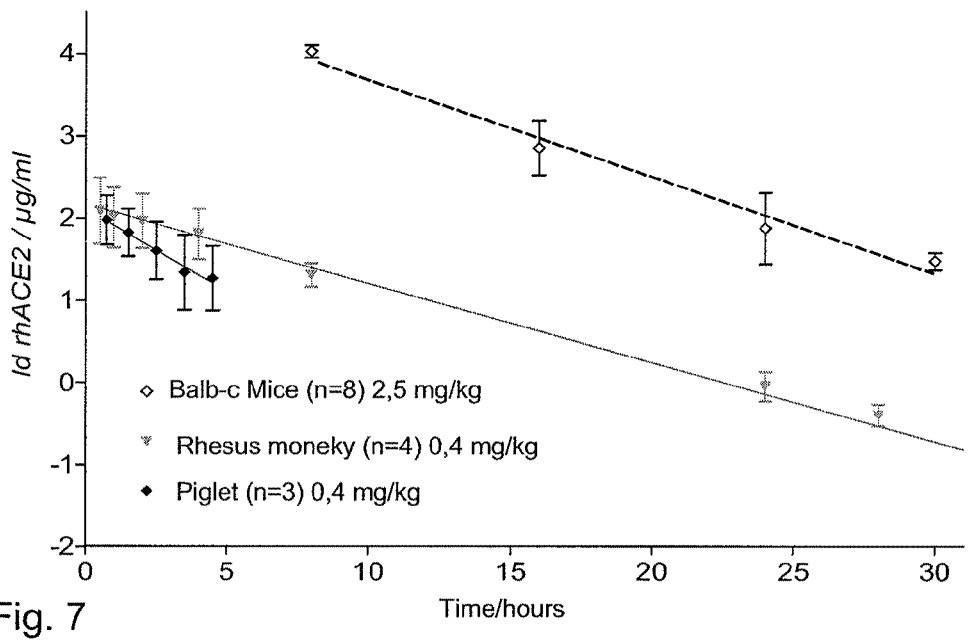
Fig. 7
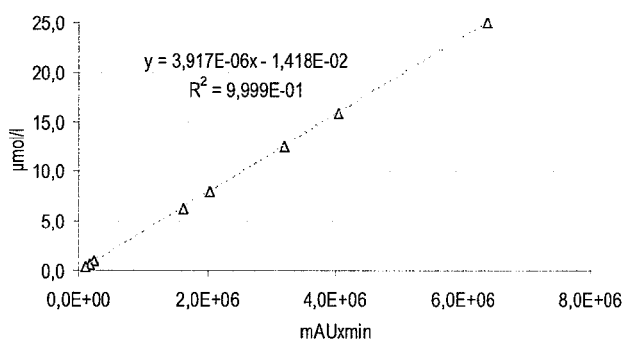
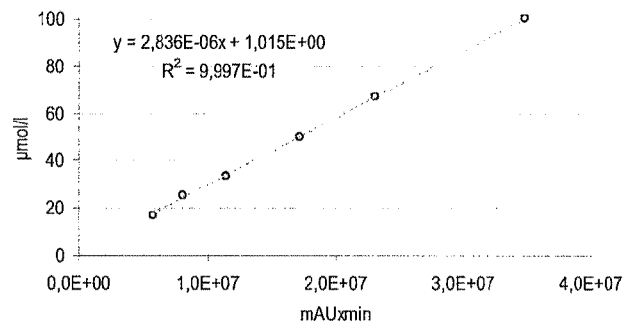
Fig. 8

Fig. 10

Name: Sequence length: 740
```
MSSSSWLLLS LVAVTAAQST IEEQAKTFLD KFNHEAEDLF YQSSLASWNY NTNITEENVQ NMNNAGDKWS AFLKEQSTLA
QMYPLQEIQN LTVKLQLQAL QQNGSSVLSE DKSKRLNTIL NTMSTIYSTG KVCNPDNPQE CLLLEPGLNE IMANSLDYNE
RLWAWESWRS EVGKQLRPLY EEYVVLKNEM ARANHYEDYG DYWRGDYEVN GVDGYDYSRG QLIEDVEHTF EEIKPLYEHL
HAYVRAKLMN AYPSYISPIG CLPAHLLGDM WGRFWTNLYS LTVPFGQKPN IDVTDAMVDQ AWDAQRIFKE AEKFVSVGL
PNMTQGFWEN SMLTDPGNVQ KAVCHPTAWD LGKGDFRILM CTKVTMDDFL TAHHEMGHIQ YDMAYAAQPF LLRNGANEGF
HEAVGEIMSL SAATPKHLKS IGLLSPDFQE DNETEINFLL KQALTIVGTL PFTYMLEKWR WMVFKGEIPK DQWMKKWWEM
KREIVGVVEP VPHDETYCDP ASLFHVSNDY SFIRYYTRTL YQFQFQEALC QAAKHEGPLH KCDISNSTEA GQKLFNMLRL
GKSEPWTLAL ENVVGAKNMN VRPLLNYFEP LFTWLKDQNK NSFVGWSTDW SPYADQSIKV RISLKSALGD KAYEWNDNEM
YLFRSSVAYA MRQYFLKVKN QMILFGEEDV RVANLKPRIS FNFFVTAPKN VSDIIPRTEV EKAIRMSRSR INDAFRLNDN
SLEFLGIQPT LGPPNQPPVS
```

| SeqName | Position | Potential | Jury-agreement | N-Glyc result | |
|---|---|---|---|---|---|
| sequence | 53 NITE | 0.7657 | (9/9) | +++ | |
| sequence | 90 NLTV | 0.7079 | (9/9) | ++ | YES |
| sequence | 103 NGSS | 0.7036 | (9/9) | ++ | YES |
| sequence | 322 NMTQ | 0.6642 | (9/9) | ++ | |
| sequence | 432 NETE | 0.7101 | (7/9) | + | YES |
| sequence | 546 NSTE | 0.4684 | (5/9) | - | YES |
| sequence | 690 NVSD | 0.5851 | (7/9) | + | YES |

Fig. 14

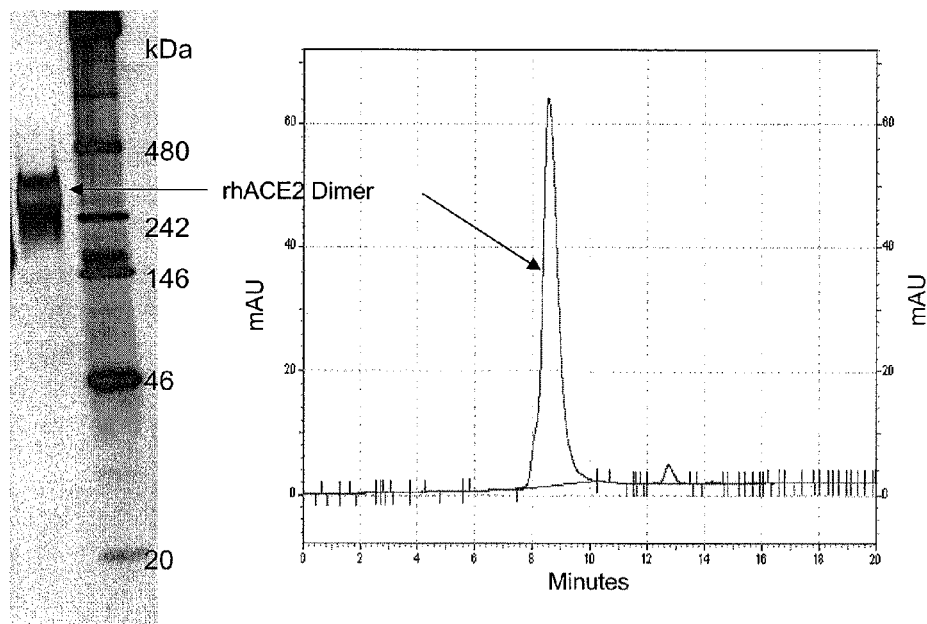

RECOMBINANT ACE2 POLYPEPTIDE DIMER

This application is a national phase application under 35 U.S.C. §371 of International Application No. PCT/AT2008/000211 filed 12 Jun. 2008, which claims priority to Austrian Application No. A 913/2007 filed 12 Jun. 2007 and European Application No. 08450052.9 filed 8 Apr. 2008. The entire text of each of the above-referenced disclosures is specifically incorporated herein by reference without disclaimer.

The present invention relates to the field of recombinant protein production.

Angiotensin converting enzyme (ACE2) is a key enzyme in the renin-angiotensin system. It is anchored to the membrane as a carboxypeptidase, and expressed as a receptor primarily in lung, kidney and heart cells, but also on endothelial cells and cleaves various peptide substrates. Prominent representatives of the substrates are angiotensin II (Ang II), which is cleaved to angiotensin 1-7 (Ang 1-7), angiotensin I, which is cleaved to angiotensin 1-9, and also apelin and bradykinin. Ang II and Ang 1-7 are antagonists of the renin-angiotensin system. By controlling peptide ratios, ACE2 is responsible for regulating vessel thickness and for endothelial permeability, thereby influencing homeostatis of the organism. ACE2 expression is zytokine-controlled, inter alia, and is decreased in various inflammatory diseases which subsequently results in a pathological enrichment of Ang II, one of the most important substrates for ACE2.

ACE2 is used to treat ARDS or ALI, two forms of an acute lung disease which is associated with down-regulated ACE2 expression in the lung. This therapy uses recombinant soluble human ACE2 which is administered systemically and is very quickly available to the entire organism in order to reduce a raised concentration of Ang II and thus to produce Ang 1-7. This compensates for the negative effects of increased Ang II concentrations. In this case, it would be desirable to have available a product which has a suitable pharmacological profile: accordingly, a suitable substance would be characterized by good distribution in the organism, a pharmacologically useful half time as well as low immunogenicity. In particular, the product must be enzymatically active, have good solubility and also be stable in solution and be capable of being reproducibly and economically produced with high purity.

Tipnis et al (J Biol Chem 275, (43) (2000): 33238-43) describes the isolation of ACE2 (in that case still referred to as ACEH) and its cDNA isolation. By carrying out the production in CHO cells, a glycosylated protein monomer was produced with a molecular mass of 120 kDa. After deglycosylation, the mass of that protein was 85 kDa.

Donoghue (Circ Res 87, (5) (2000): 1-9) describes the expression of soluble ACE2 in CHO cells; it was not fully glycosylated and was characterized as having a molecular mass of approximately 90 kDa. Furthermore, that document concerns sequence comparisons of various ACE2 sequences and anti-ACE2 antibodies.

WO 2004/023270 A2 describes the crystallization of ACE2 after expression of ACE2 monomers in Sf9 insect cells. The molecular mass of the protein was given as 89.6 kDa following analysis by mass spectrometry.

The therapeutic action of an efficient enzyme substitution therapy demands a production process which can produce a very pure, pharmacologically efficient product economically and reproducibly. The soluble, extra-cellular fraction of ACE2 contains 7 N-glycosylation sites. Non-glycosylated ACE2 has low solubility, tends towards aggregation, is more immunogenic and has a shortened half time. In addition, it has a smaller hydrodynamic diameter which primarily has a deleterious effect on purification. Thus, one aim of the present invention is to provide highly active ACE2 with a good in vivo half time. This aim is achieved by the subject matter of the claims.

The present invention concerns a recombinant ACE2 polypeptide which is present as a dimer. Preferably, the recombinant ACE2 polypeptide is glycosylated, wherein the glycosyl groups of an ACE2 polypeptide monomer are present in a total of at least 10, 11, 12, 13, 14, 15 or at least 16 sialic acid residues, preferably at least 14 sialic acid residues, and wherein the ACE2 polypeptide is present as a dimer. The present invention also encompasses an ACE2 monomer with the glycosylations, molecular weights and further specifications defined herein. The dimer is preferably a homo-dimer; in particular, its monomer units have an identical sequence and glycosylation. In general, the monomer units of the dimer are non-covalently bound. A monomer can be obtained directly from the dimer or by denaturing steps. All of the preferred glycosylations cited herein are applicable to both the dimer and the monomer, including one or both monomers of the dimeric complex. Particularly preferably, the dimer contains two zinc ions.

The term "sialic acid residues" means residues of the N-acetylneuraminic acid type (Neu5Ac) in particular, especially N- or O-glycosylations.

Basically, the stability of a therapeuticum is a very important criterion when considering its half time and thus its effectiveness.

Recombinant human ACE2 has until now been identified exclusively as a monomer and has been described as such in the literature as regards its functionality, its crystal structure and also its interaction with a highly specific inhibitor.

Thus, for example, Towler et al (J Biol Chem 279(17), 2004: 17996-18007), making reference to Vickers et al (J Biol Chem 277 (17), 2002: 14838-14843), describe the expression of ACE2 in Sf9 insect cells, which was obtained as a monomer following purifying size exclusion chromatography as the final purification step. The molecular mass of a monomer was 89.6 kDa.

Commercially available ACE2 (from R&D Systems, catalogue number 933-ZN, batch number FIU035071) is also in the monomeric form and is produced using the method cited in Tipnis et al (2000, supra), the difference being that the expression system is NS0 instead of CHO cells. Monomers were described which have a molecular weight of 120 kDa under both reducing and non-reducing conditions.

According to Donoghue et al (Circ Res 87, 2000: e1-e9), ACE2 monomers were expressed in CHO cells, which following secretion had a molecular weight of 90 kDa.

All of the documents and publications cited herein are hereby incorporated by reference.

In order to stabilize the therapeuticum according to the invention, in accordance with the invention a method has been developed which exclusively produces stable ACE2 dimers, and which benefits from both production and pharmacological advantages compared with ACE2 monomers.

Dimerization has the following advantages:
- better solubility and bioavailability in physiological solutions: the dimer has high solubility and a longer in vivo half time and availability;
- no aggregate formation: the ACE2 dimer forms stable complexes without addition of further ACE2 molecules to the dimer;
- reduced protease attack: since individual protein fractions and thus most probably the C-terminal portion, are directed towards the interior of the dimer, this C-terminal end is not degraded;
- increased half time: the lower immunogenicity, better solubility and the reduced susceptibility to proteolytic degradation increases the half time of the protein;
- simpler protein purification: the hydrodynamic diameter of the ACE2 dimer is higher than expected due to its structure and a pronounced solvation sheath. Thus, ACE2 dimers can readily be separated from conventional impurities arising from protein expression, for example serum albumin (67 kDa), by using size separation columns.

Preferably, the recombinant ACE2 polypeptide is glycosylated on at least 80% of the possible N-glycosylation sites and has a proportion of sugar of more than 10% (weight % of total ACE2) or 11%, 12%, 13%, 14%, preferably more than 15% or 16%, 17%, 18%, 19%, in particular more than 20% or 21%, 22%, 23%, 24% or 25%.

A production method has been developed which reproducibly produces very pure and enzymatically active, highly complexed glycosylated ACE2. The product is characterized by its high proportion of sugar (>20% by weight) and the complex, highly branched, partially negatively charged sugar structures. These have a positive effect on solubility, bioavailability, enzymatic activity as well as the pharmacological properties of the product. By selecting a suitable expression construct, a suitable expression host, an optimized selection strategy, using a medium which is tailored for the cell metabolism as well as painstaking accompanying clone analysis and selection, a cell line has been able to be produced which secretes the desired product.

ACE2 has already been expressed in Sf9 insect cells and NS0 mouse cells. The material was primarily used in in vitro trials. There also exist results regarding the transient expression of ACE2 in CHO cells. Until now, no cell lines have been produced with a suitably high productivity. Further, no corresponding clone selection has yet been carried out concerning the product's properties, in particular having regard to N-glycosylation.

The solubility of a protein is not only determined by means of its amino acid sequence, but also by its folding as well as post-translational modifications. Charged sugar structures are the main cause of an increase in the solubility of a protein and have a major influence on its pharmacological profile. Thus, it has been shown for EPO that the presence of complex branched glycostructures has a positive effect on the half time of this protein.

In principle, various expression systems can be considered for the recombinant expression of ACE2; prokaryotic host cells have not been tested further because of the lack of processing of N-glycosylation sites.

Preferably, at least 70% of the glycosylated N-glycosylation sites have a structure, independently of each other, selected from formulae 1 to 8:

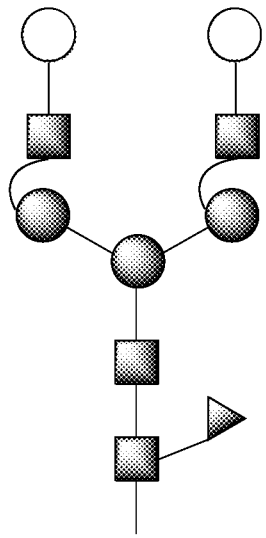

(formula 1)

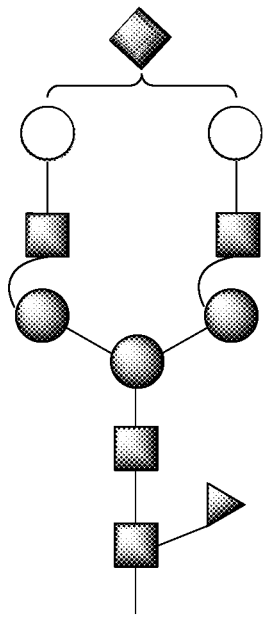

(formula 2)

(formula 3)
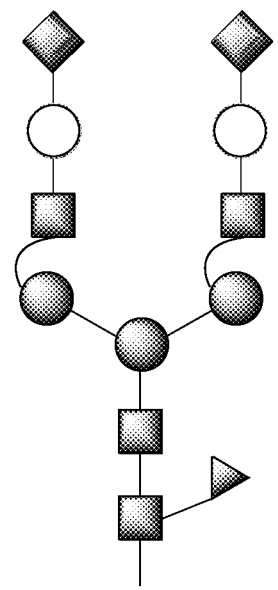
(formula 5)
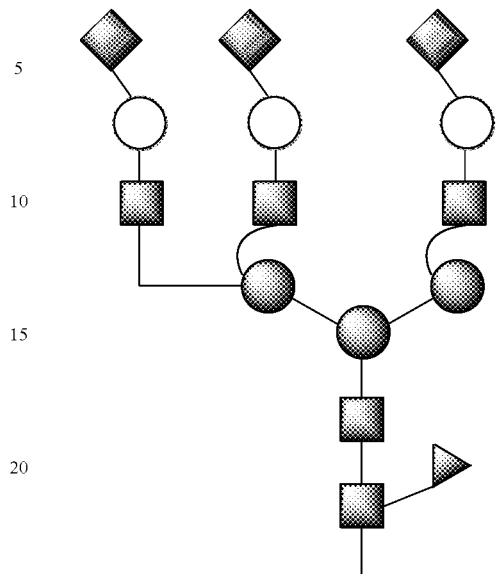
(formula 4)
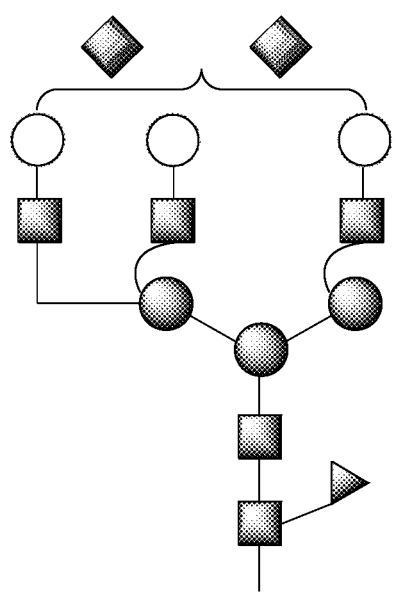
(formula 7)
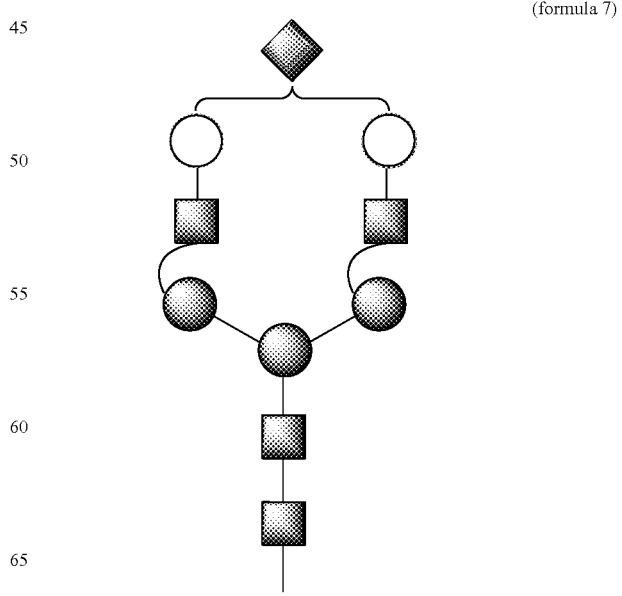

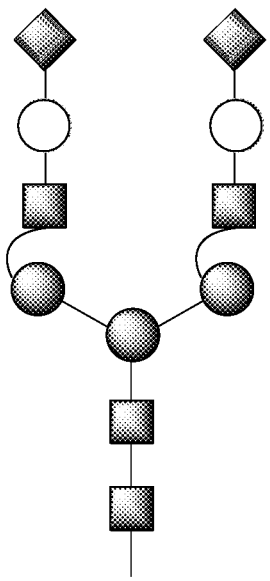

(formula 8)

in which:

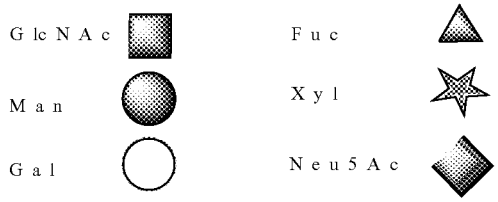

Preferably, all of the possible N-glycosylation sites are glycosylated.

Preferably, at least 80%, preferably at least 90%, in particular 100% of the glycosylated N-glycosylation sites have a structure with formulae 1-8.

Preferably, one ACE2 monomer unit of the dimer has a molecular weight of at least 90 kDa, preferably at least 92 kDa, particularly preferably at least 94 kDa, in particular at least 96 kDa, and highly preferably at least 98 kDa, most preferably at least 100 kDa, 100.5 kDa, 101 kDa, 101.5 kDa or at least 102 kDa. An absolute molecular mass—i.e. of the peptide per se without the hydrate sheath—can be determined by peptide mapping. More highly glycosylated forms may also have molecular masses of at least 103 kDa, 104 kDa, 105 kDa, 106 kDa, 107 kDa or at least 108 kDa.

Molecular weight determinations which are influenced by further factors such as the hydrate sheath, such as chromatography or gel electrophoresis in aqueous systems—can also give higher results. In further embodiments, an ACE2 monomer unit of the dimer has an apparent molecular weight of at least 101 kDa or at least 102 kDa, preferably at least 105 kDa, particularly preferably at least 109 kDa, in particular at least 113 kDa, and highly preferably at least 117 kDa, and most preferably at least 119 kDa, as determined by gel electrophoresis.

In other embodiments, the molecular weight of the monomer (apparent or absolute) is a maximum of 102 kDa, 103 kDa, 104 kDa, 108 kDa, 110 kDa, 112 kDa, 116 kDa, 120 kDa, 125 kDa, 130 kDa, 135 kDa or 140 kDa. Higher molecular weights are possible by modification of ACE2, for example PEGylation.

Preferably, the monomer (which does not form a dimer) has a molecular weight of at least 82 kDa, preferably at least 86 kDa, particularly preferably at least 90 kDa, in particular at least 94 kDa, highly preferably at least 98 kDa, and most preferably at least 101 kDa or a maximum of 102 kDa, 103 kDa, 104 kDa, 108 kDa, 110 kDa or a maximum of 112 kDa. These molecular weights can be determined, for example, using the peptide mapping method.

Preferably, the ACE2 polypeptide has no trans-membrane domains. Thus, it is soluble ACE2. Particularly preferred embodiments thus comprise soluble ACE2 polypeptides the polypeptide chains of which consist of amino acids 18-740 or enzymatically active fragments thereof. A further polypeptide consists of amino acids 18-615 from SEQ ID NO: 1.

Although human ACE2 (SEQ ID NO: 1) is preferred for most therapeutic applications, ACE2 from other mammals, for example mouse, rat, hamster, pig, primates or cattle, can also be used. ACE2 is a universal enzyme in all mammals with the Ang II substrate which is identical in the various species. Hence, in principle it can also be used in foreign organisms. Thus, the protein according to the invention can be used regardless of the origin of the ACE2, for example from humans, mice, rats, hamsters, pigs, primates or cattle. However, in preferred embodiments, the origin of the ACE2 and the organism to be treated is the same.

Preferably, a serine (or C-terminal amino acid) of the ACE2 polypeptide corresponding to Ser740 of SEQ ID NO: 1 (for example the C-terminal end) is O-glycosylated.

Preferably, at least 70%, preferably at least 80%, in particular at least 90%, and most preferably 100% of the glycosylated N-glycosylation sites exhibit sialic acid; preferably, the N-glycosylation sites corresponding to Asn53, Asn90, Asn103, Asn322, Asn432, Asn546, Asn690 of SEQ ID NO: 1 are sialyzed.

In specific embodiments, an asparagin corresponding to Asn53 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn90 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn103 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn322 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn432 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn546 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Asn690 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

In specific embodiments, an asparagin corresponding to Ser740 of SEQ ID NO: 1 is mono-, bi-, tri- or tetra-sialyzed. Preferably, in one ACE2 preparation at least 50%, 60%, 70%, 80%, 90%, 95%, 99% or 100% of said amino acids are either mono-, bi-, tri- or tetra-sialyzed.

Preferably, at least 30%, preferably at least 40%, in particular at least 55% and most preferably at least 70% of the glycosylated N-glycosylation sites have at least two sialic acids. Preferably, in one ACE2 preparation at least 50%, 60%, 70%, 80%, 90%, 95%, 99% or 100% of said amino acids are thus sialyzed.

Preferably, an asparagin corresponding to Asn53 of SEQ ID NO: 1 is N-glycosylated, preferably with a glycan having a structure in accordance with formula 1, 2, 3, 4, 5, 6, 7 or 8.

Preferably, an asparagin corresponding to Asn90 of SEQ ID NO: 1 is N-glycosylated, preferably with a glycan having a structure in accordance with formula 1, 2, 3, 4, 5, 6, 7 or 8.

Preferably, an asparagin corresponding to Asn103 of SEQ ID NO: 1 is N-glycosylated, preferably with a glycan having a structure in accordance with formula 1, 2, 3, 4, 5, 6, 7 or 8.

Preferably, an asparagin corresponding to Asn322 of SEQ ID NO: 1 is N-glycosylated, preferably with a glycan having a structure in accordance with formula 1, 2, 3, 4, 5, 6, 7 or 8.

Preferably, an asparagin corresponding to Asn432 of SEQ ID NO: 1 is N-glycosylated, preferably with a glycan having a structure in accordance with formula 1, 2, 3, 4, 5, 6, 7 or 8.

Preferably, an asparagin corresponding to Asn546 of SEQ ID NO: 1 is N-glycosylated, preferably with a glycan having a structure in accordance with formula 1, 2, 3, 4, 5, 6, 7 or 8.

Preferably, an asparagin corresponding to Asn690 of SEQ ID NO: 1 is N-glycosylated, preferably with a glycan having a structure in accordance with formula 1, 2, 3, 4, 5, 6, 7 or 8.

In a further aspect, the present invention concerns a preparation of recombinant ACE2 polypeptides, comprising a polypeptide as defined herein (ACE2 monomers or dimers or monomer units of dimers), wherein the portion of ACE2 polypeptides with an apparent molecular weight which can be determined by gel electrophoresis of less than 100 kDa or less than 101 kDa, preferably less than 104 kDa, highly preferably less than 108 kDa, in particular less than 112 kDa, particularly preferably less than 117 kDa, most preferably less than 119 kDa, is less than 20%, preferably less than 10%, particularly preferably less than 5%, most preferably less than 1%, especially 0%, and any combination thereof. For example, ACE2 polypeptides of less than 100 kD may be present in an amount of 0% and ACE2 polypeptides of less than 100 kDa may be present in an amount of less than 20%. The fraction is with respect to all of the ACE2 forms involved and is, for example, determined using native gel electrophoresis.

Similarly, the molecular mass may be the absolute molecular mass which can be determined by peptide mapping. Thus, the fraction of ACE2 polypeptides with a molecular weight of less than 86 kDa, or less than 89 kDa, preferably less than 92 kDa, highly preferably less than 94 kDa, in particular less than 97 kDa, particular preferably less than 100 kDa, and most preferably less than 101 kDa, is less than 20%, preferably less than 10%, particularly preferably less than 5%, most preferably less than 1%, especially 0%, and any combination thereof. For example, ACE2 polypeptides of less than 86 kD may be present in an amount of 0%; and ACE2 polypeptides of less than 97 kDa may be present in an amount of less than 20%.

Preferably, the fraction of ACE2 polypeptides with transmembrane domains is less than 20%, preferably less than 10%, particularly preferably less than 5%, most preferably less than 1%, especially 0%.

Preferably, the fraction of ACE2 multimers is less than 20%, preferably less than 10%, particularly preferably less than 5%, most preferably less than 1%, especially 0%. The term "ACE2 multimers" means complexes with 3 or more ACE2 polypeptides. In addition, in a preparation of ACE2 dimers, the fraction of ACE2 monomers is preferably less than 20%, preferably less than 10%, particularly preferably less than 5%, most preferably less than 1%, especially 0%. In addition, in a preparation of ACE2 monomers, the fraction of ACE2 dimers is preferably less than 20%, preferably less than 10%, particularly preferably less than 5%, most preferably less than 1%, especially 0%.

Preferably, the fraction of ACE2 dimers in ACE2 molecules is at least 10%, 20%, 30%, 40%, 50%, 60%, 70%, 80%, 90%, 95% or at least 99%. In further embodiments, in combination there-with or independently, the fraction of ACE2 monomers in ACE2 molecules can be at least 10%, 20%, 30%, 40%, 50%, 60%, 70%, 80%, 90%, 95% or at least 99%.

Preferably, the fraction of ACE2 polypeptides with N-glycosylated asparagin corresponding to Asn53 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn90 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn103 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn322 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn432 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn546 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with N-glycosylated asparagin corresponding to Asn690 of SEQ ID NO: 1 is more than 60%, preferably more than 70%, particularly preferably more than 80%, highly preferably more than 90%, most preferably more than 99%, and especially 100%, and preferably with a glycan having a structure in accordance with formulae 1, 2, 3, 4, 5, 6, 7 or 8.

Preferably, the fraction of ACE2 polypeptides with O-glycosylated asparagin corresponding to Ser740 of SEQ ID NO: 1 is more than 60%, preferably more than 70%, particularly preferably more than 80%, highly preferably more than 90%, most preferably more than 99%, and especially 100%.

Preferably, the catalytic activity of the ACE2 polypeptide or preparation, ccat, is at least $4\ s^{-1}$, preferably at least $5\ s^{-1}$, particularly preferably at least $6\ s^{-1}$, highly preferably at least $7\ s^{-1}$, and most preferably at least $7.6\ s^{-1}$ with respect to the Ang 1-7 (angiotensin 1-7) conversion. Ang 1-7 is formed from Ang II (angiotensin II) by means of ACE2. The conversion can be tested in a simple manner, as described in the examples. This conversion or the catalytic activity of ACE2 can also be extrapolated from other assay data. The activity can, for example, be measured as described in WO-2008/046125 A.

In a further aspect, the present invention concerns a method for producing recombinant ACE2 polypeptides or a preparation of recombinant ACE2, comprising the steps of bringing a polynucleotide coding for an ACE2, preferably a polynucleotide coding for an ACE2 with no transmembrane domain, into eukaryotic cells, expressing the ACE2 polypeptide and collecting the expressed ACE2, in particular in the dimeric form. The cells can then be selected in order to produce an ACE2 polypeptide in accordance with the invention as herein described, in particular with a high molecular weight.

Preferably, the polynucleotide coding for the ACE2 is provided on a vector.

Preferably, the ACE2 expression is selected with a marker, preferably DHFR. Preferably, the marker is on a vector.

Preferably, the vector has an IRES for the expressed ACE2 mRNA (or codes for it).

Preferably, the eukaryotic cells are CHO cells.

The present invention also concerns recombinant ACE2 polypeptide or a preparation of recombinant ACE2 polypeptide obtainable by such a method.

In a further aspect, the invention provides a stable eukaryotic cell line (or cell) having a transfected polynucleotide coding for an ACE2, preferably a CHO cell line (or cell) which expresses ACE2, in particular as defined above. The cell line may be selected for the desired properties, as given above, for example the production of dimers from monomer units with a molecular weight of at least 102 kDa.

The cells preferably have an ACE2 productivity of at least 10 pg/cell/day, preferably at least 15 pg/cell/day, particularly preferably at least 20 pg/cell/day.

The expression of ACE2 preferably occurs in the presence of sufficient $Zn^{2+}$ ions. Preferably, at least 0.5 micromolar, in particular up to 5 micromolar of $Zn^{2+}$ is used; in particular, the fermentation can be carried out using 2.5-3.5 micromolar $Zn^{2+}$. The $Zn^{2+}$ concentration in the nutrient medium for the expressed cells, for example, may be at least 0.5 µM, 0.75 µM, 1.0 µM, 1.25 µM, 1.5 µM, 1.75 µM, 2.0 µM, 2.25 µM or at least 2.5 µM or 3.0 µM. Further treatment steps are preferably also carried out in the presence of $Zn^{2+}$ ions.

In a further aspect, the present invention concerns medicines or pharmaceutical preparations of the ACE2 product in accordance with the invention, in particular for the treatment or prevention of high blood pressure, heart insufficiency such as congestive, acute or chronic heart insufficiency, myocardial infarction or artherosclerosis, kidney failure or insufficiency, polycystic kidney disease, PKD, or lung diseases such as chronic obstructive lung disease, pneumonia, asthma, chronic bronchitis, emphysema, cystic fibrosis, interstitial lung disease, pulmonary hypertonia, lung embolism, sarcoidosis of the lung, tuberculosis, oedema of the lung, ALI, ARDS or lung cancer. General treatment indications for ACE2 are cited in WO 2004/000367 A, for example; the ACE2 product of the invention is also suitable in this case.

In accordance with the invention, a pharmaceutical composition or medicine comprising the ACE2 protein can be provided. Such compositions may be pharmaceutically acceptable salts themselves, with additional buffers, tonicity components or pharmaceutically acceptable carriers. Pharmaceutical carrier substances serve to improve the compatibility of the composition and provide better solubility as well as better bioavailability of the active ingredients. Examples are emulsifiers, thickeners, redox components, starches, alcoholic solutions, polyethylene glycol and lipids. Selection of a suitable pharmaceutical carrier is highly dependent on the administration route. For oral administration, liquid or solid carriers may be used; for injections, liquid final compositions are required.

Preferably, the ACE2 composition in accordance with the invention comprises buffers or tonic substances. The buffer can adjust the pH of the medicine to the physiological conditions and further, can reduce or buffer variations in pH. An example is a phosphate buffer. Tonic substances can adjust the osmolarity and may include ionic substances, such as inorganic salts, for example NaCl or KCl, or non-ionic substances such as glycerin or carbohydrates.

Preferably, the composition or the medicine for use in accordance with the invention is suitably prepared for systemic, topical, oral or intranasal administration or as an inhaled preparation. These forms of administration for the composition of the present invention allow fast, uncomplicated take-up. When the ACE2 composition is intended for oral administration, it is preferably provided in a formulation which is resistant to stomach acid or it is encapsulated. For oral administration, solid or liquid medicines can be taken directly or dissolved or diluted, for example.

The medicine for use in accordance with the invention is preferably produced for intravenous, intra-arterial, intramuscular, intravascular, intraperitoneal or subcutaneous administration. Injections or transfusions, for example, are suitable for this purpose. Administration directly into the bloodstream has the advantage that the active ingredient of the medicine can be distributed through the entire body and the target tissue is reached quickly.

The present invention will now be illustrated further using the following non-limiting figures and examples.

FIGURES

Figure 3:
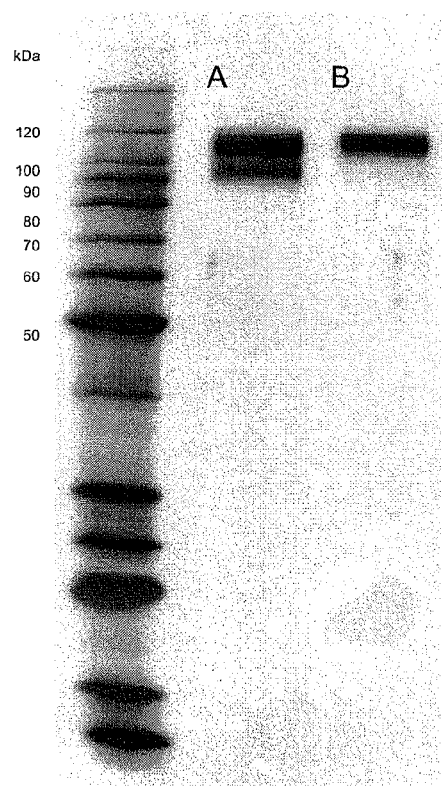
Figure 2:
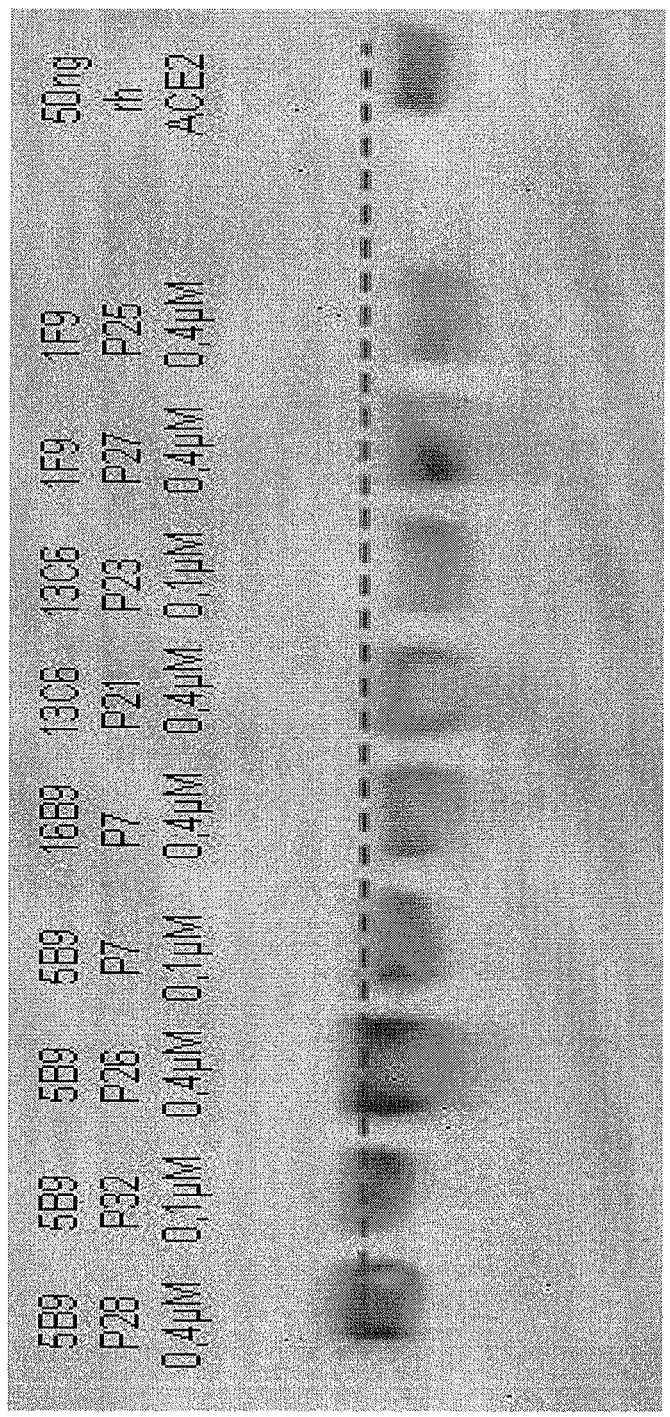
Figure 4:
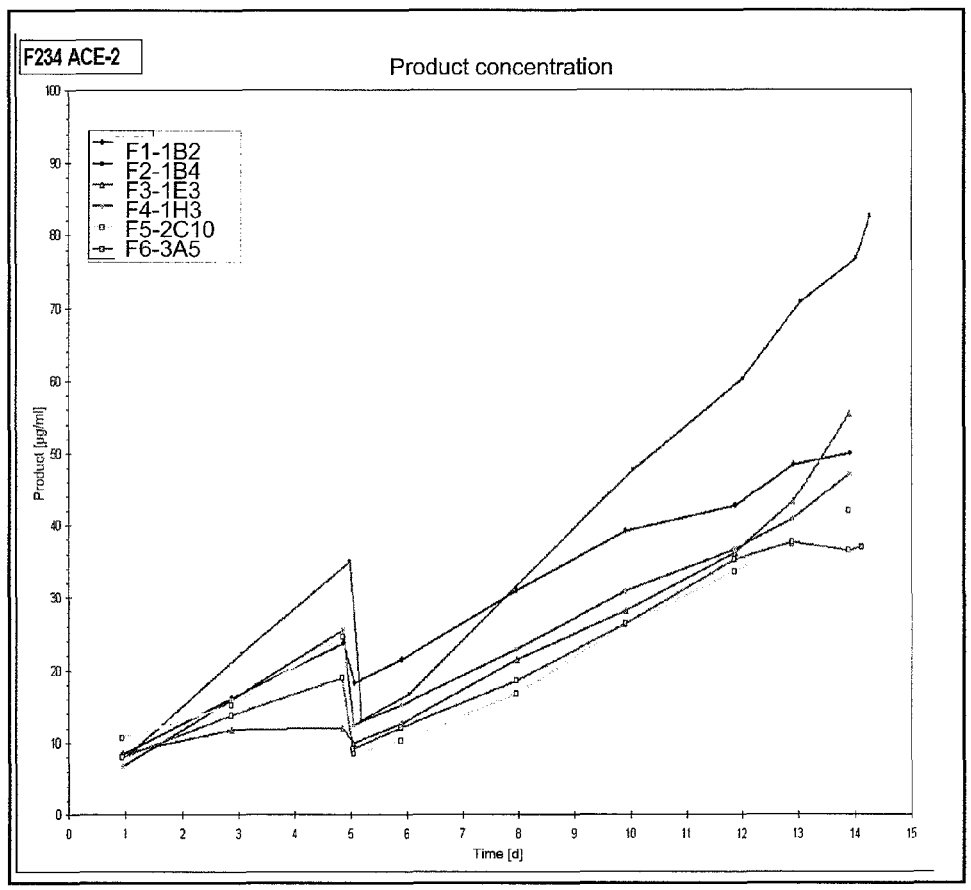
Figure 4:
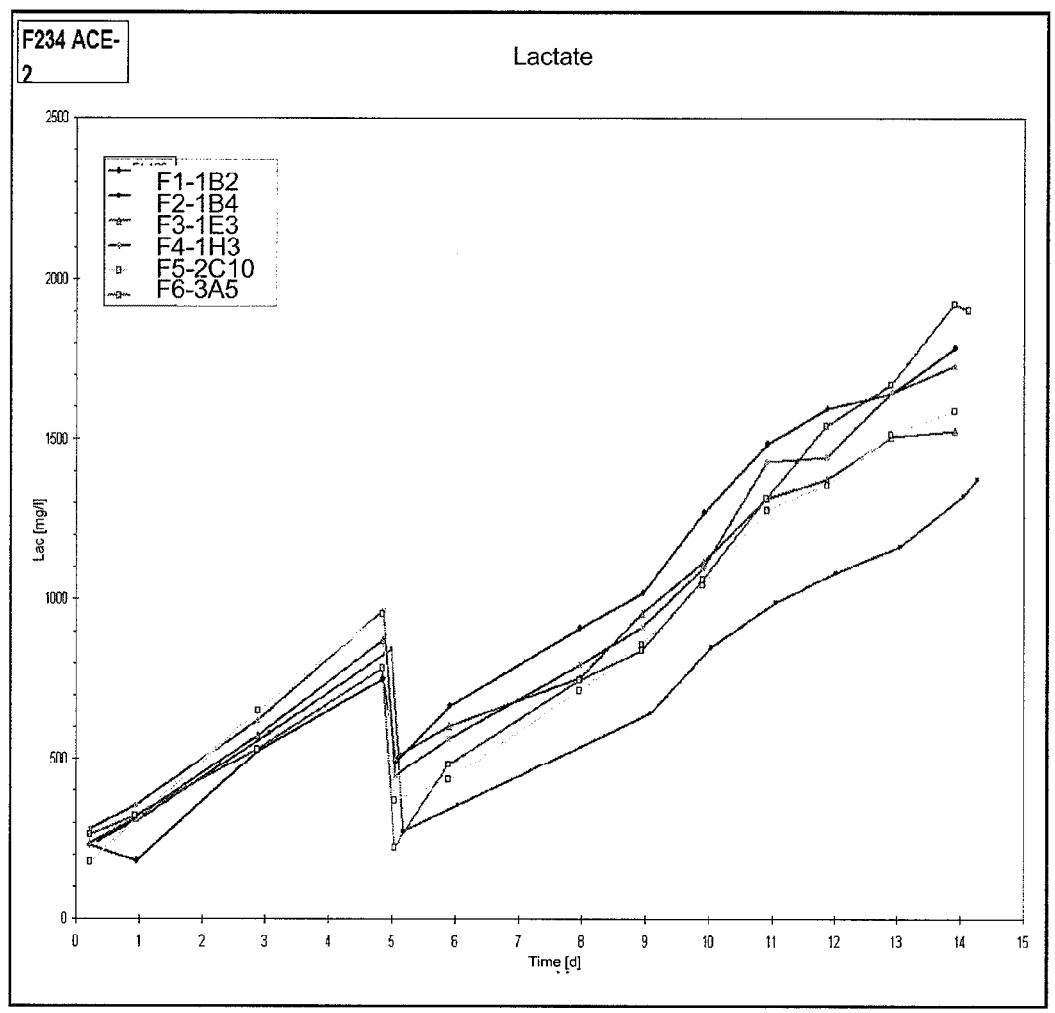
Figure 5:
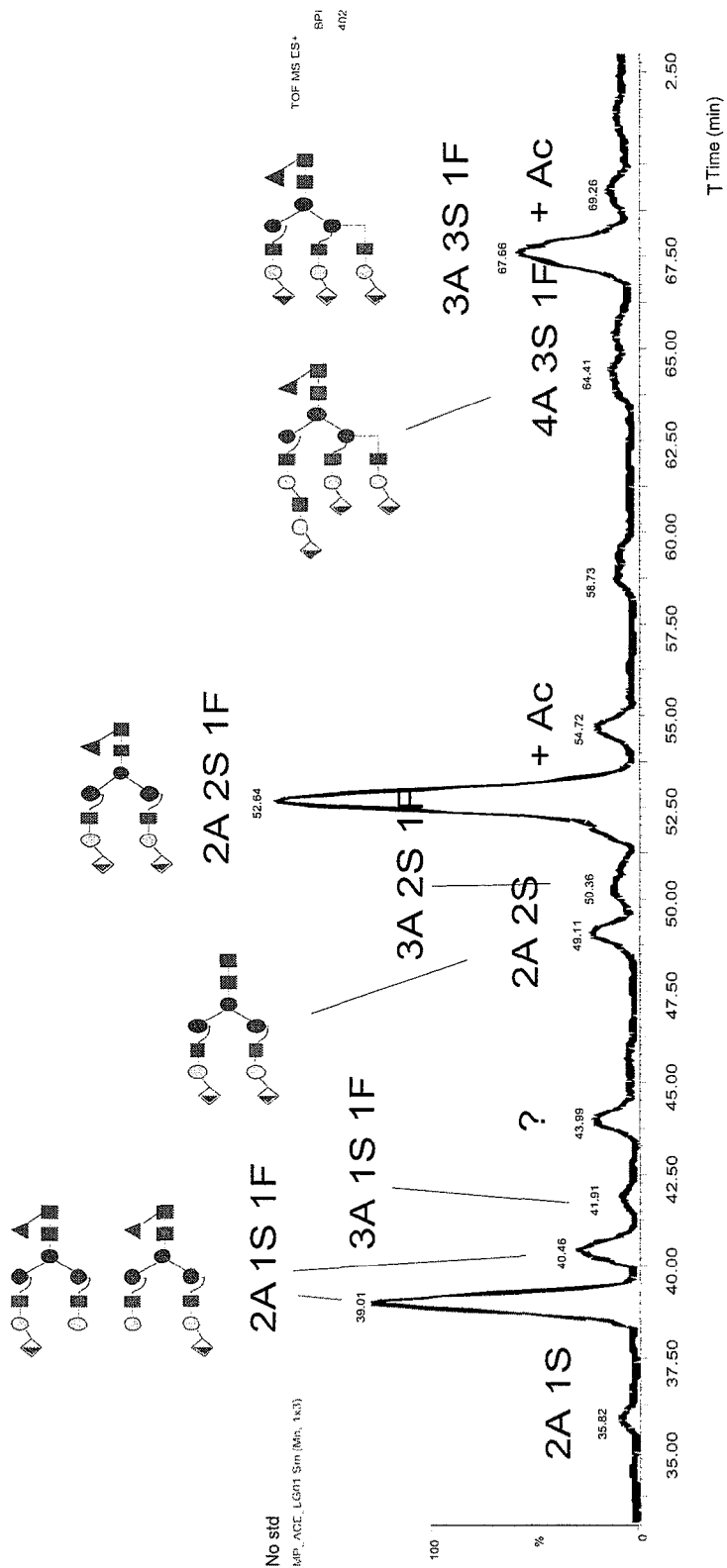
Figure 6:
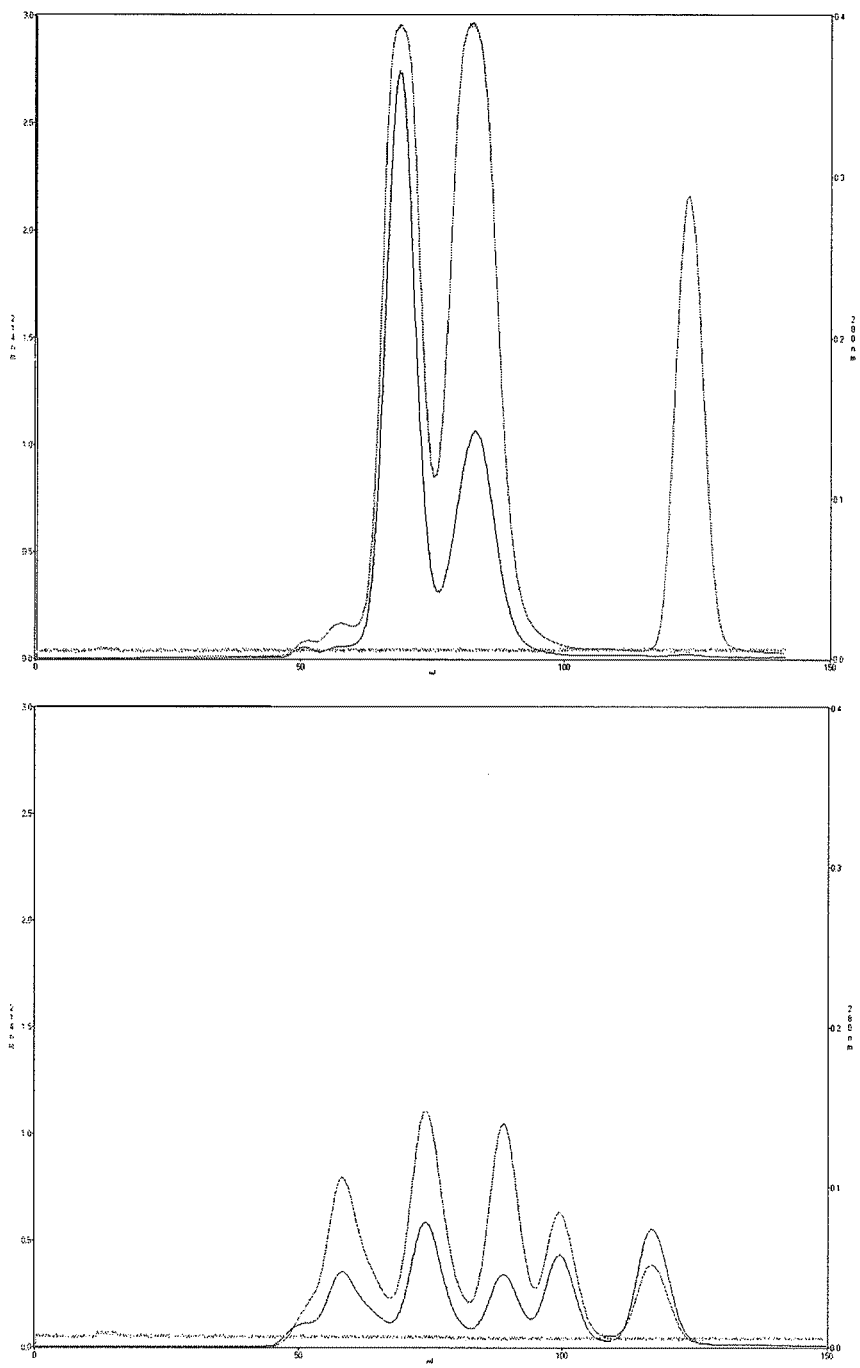
Figure 9:
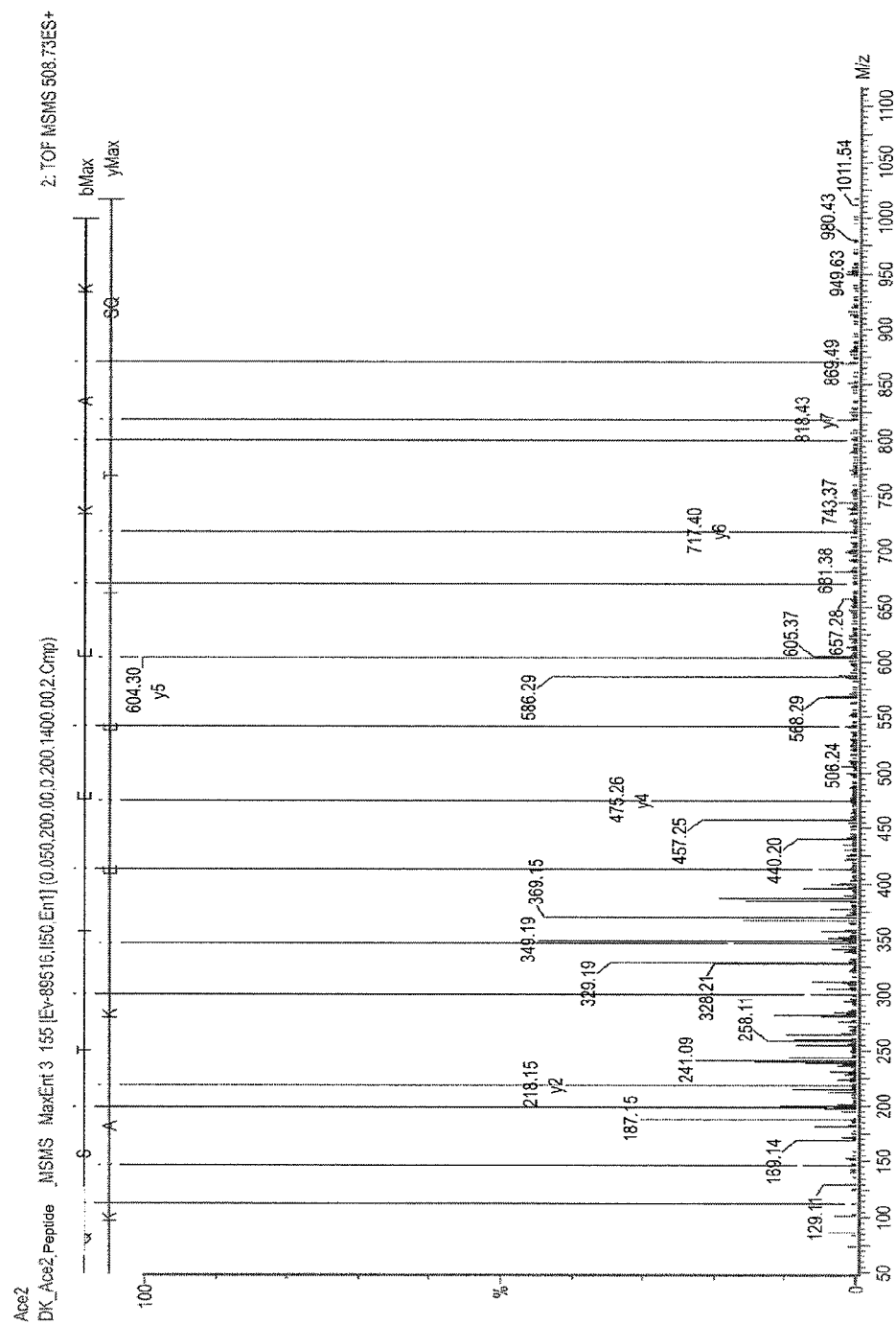
Figure 11A:
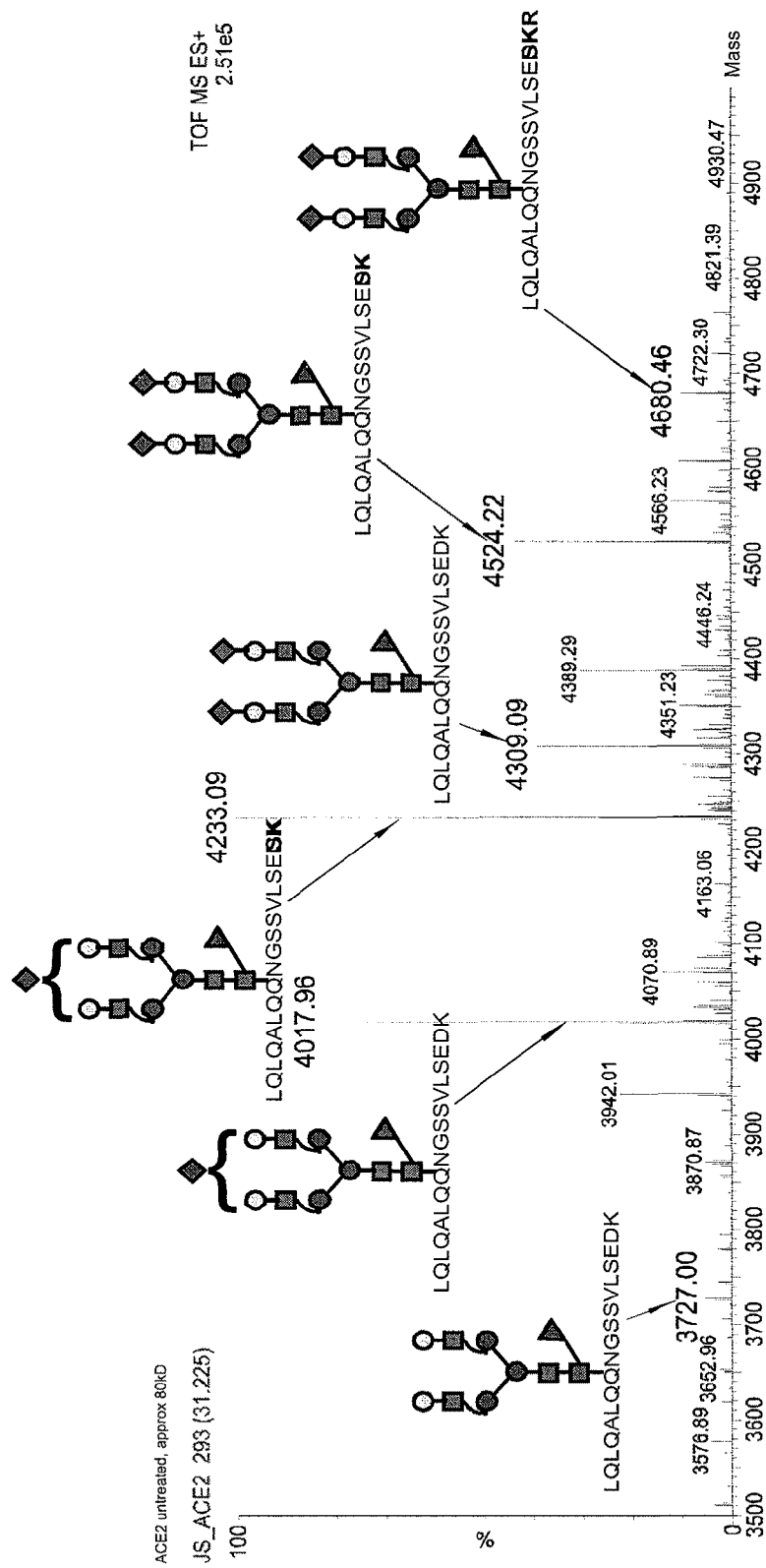
Figure 11B:
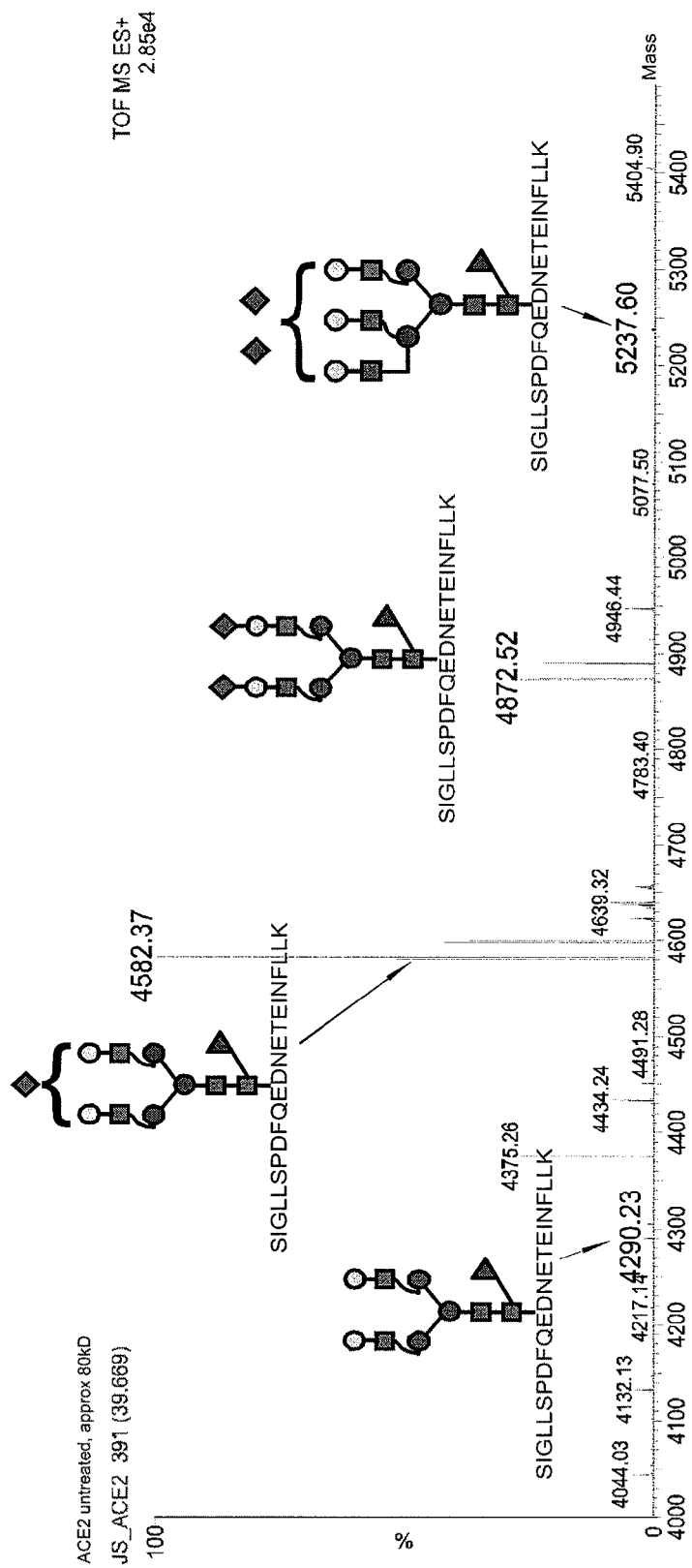
Figure 11C:
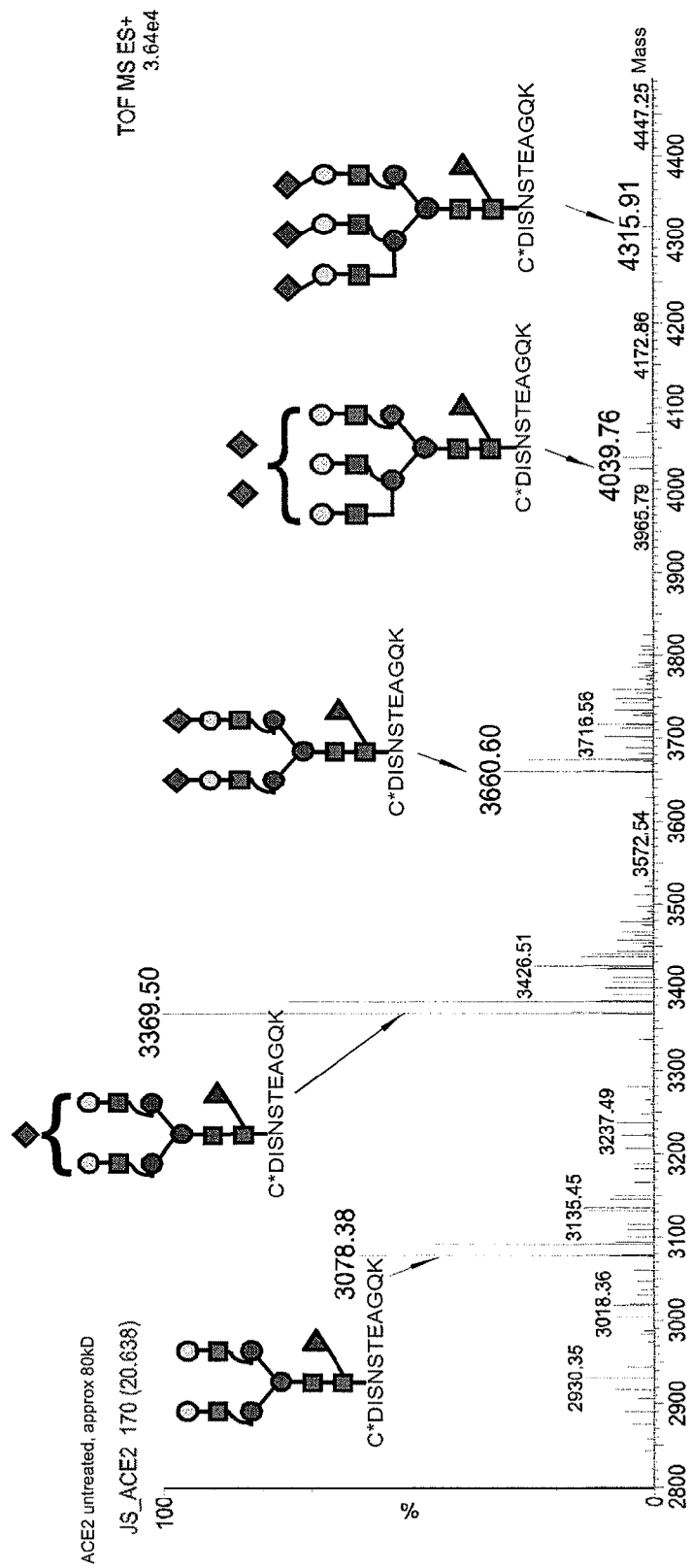
Figure 11D:
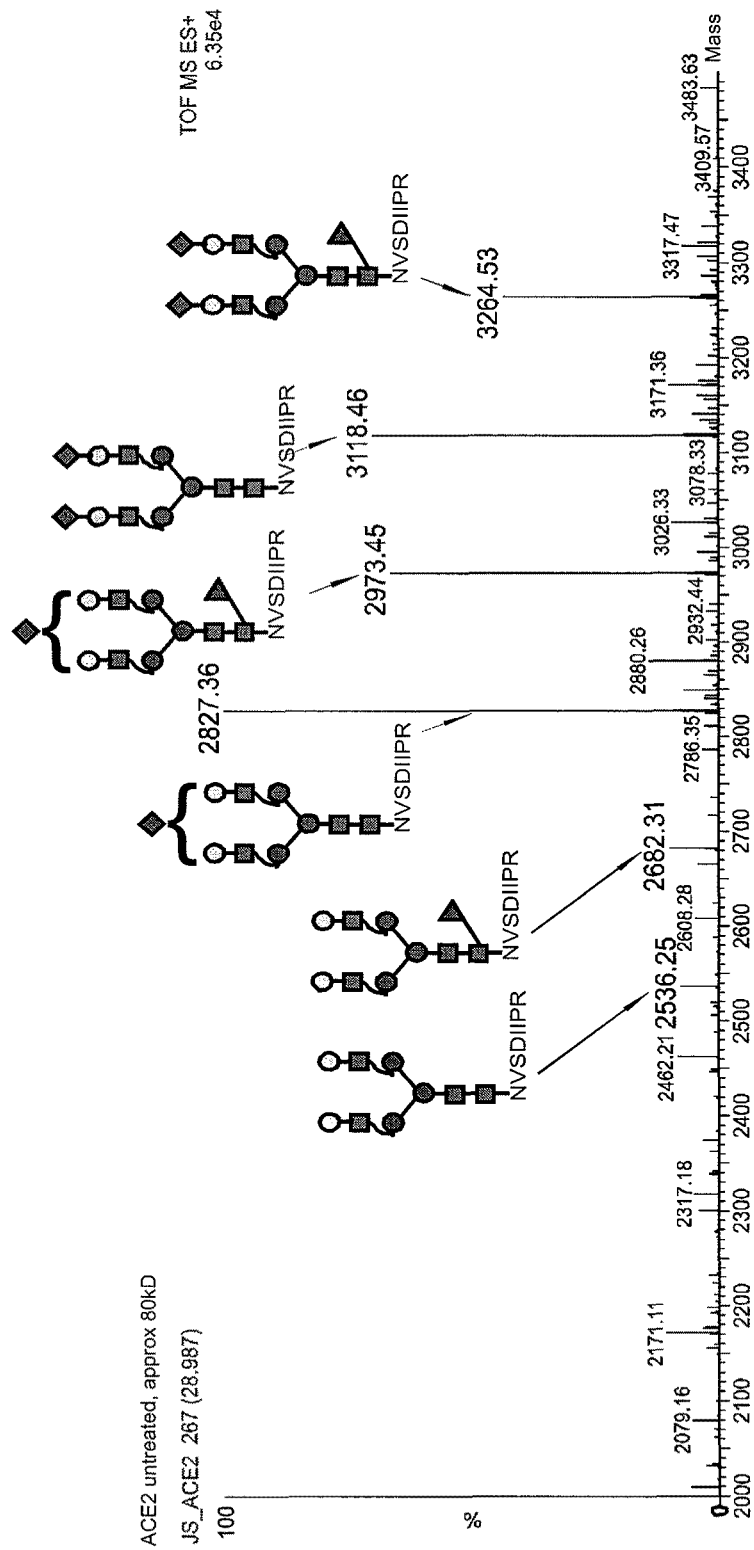
Figure 11E:
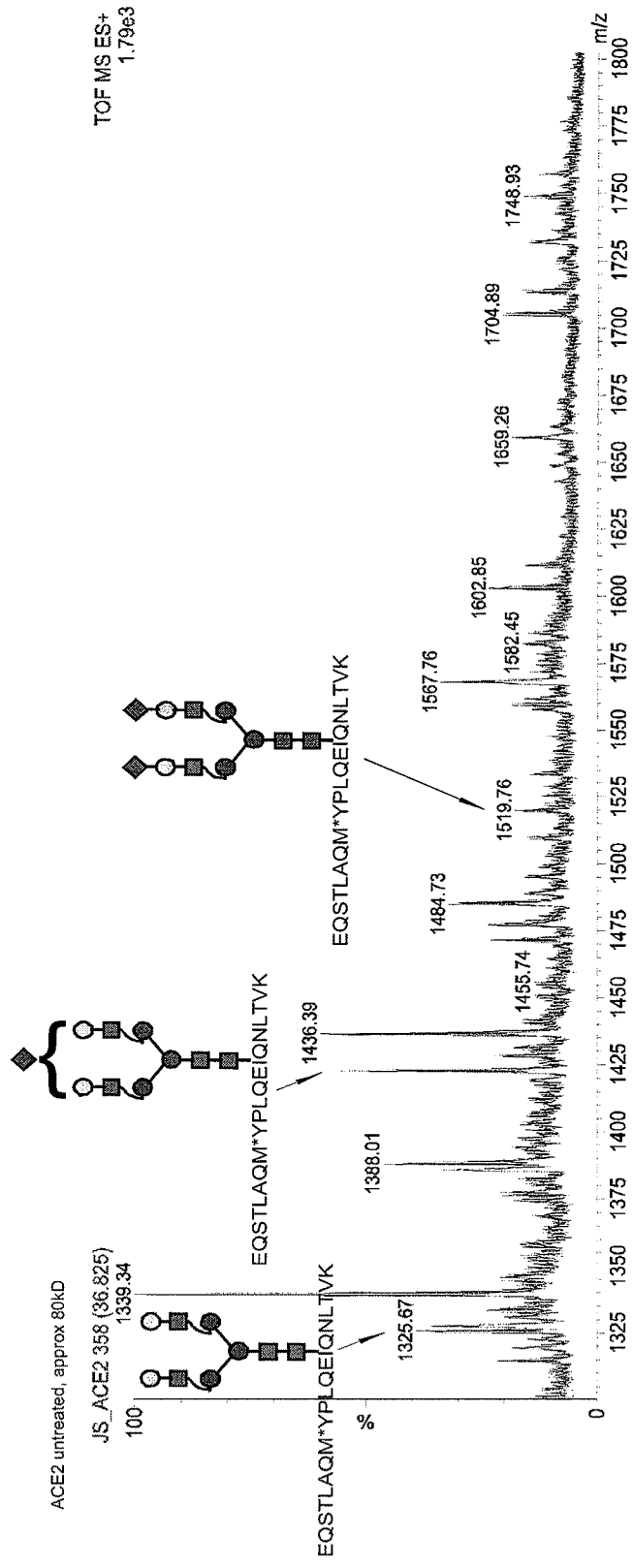
Figure 12:
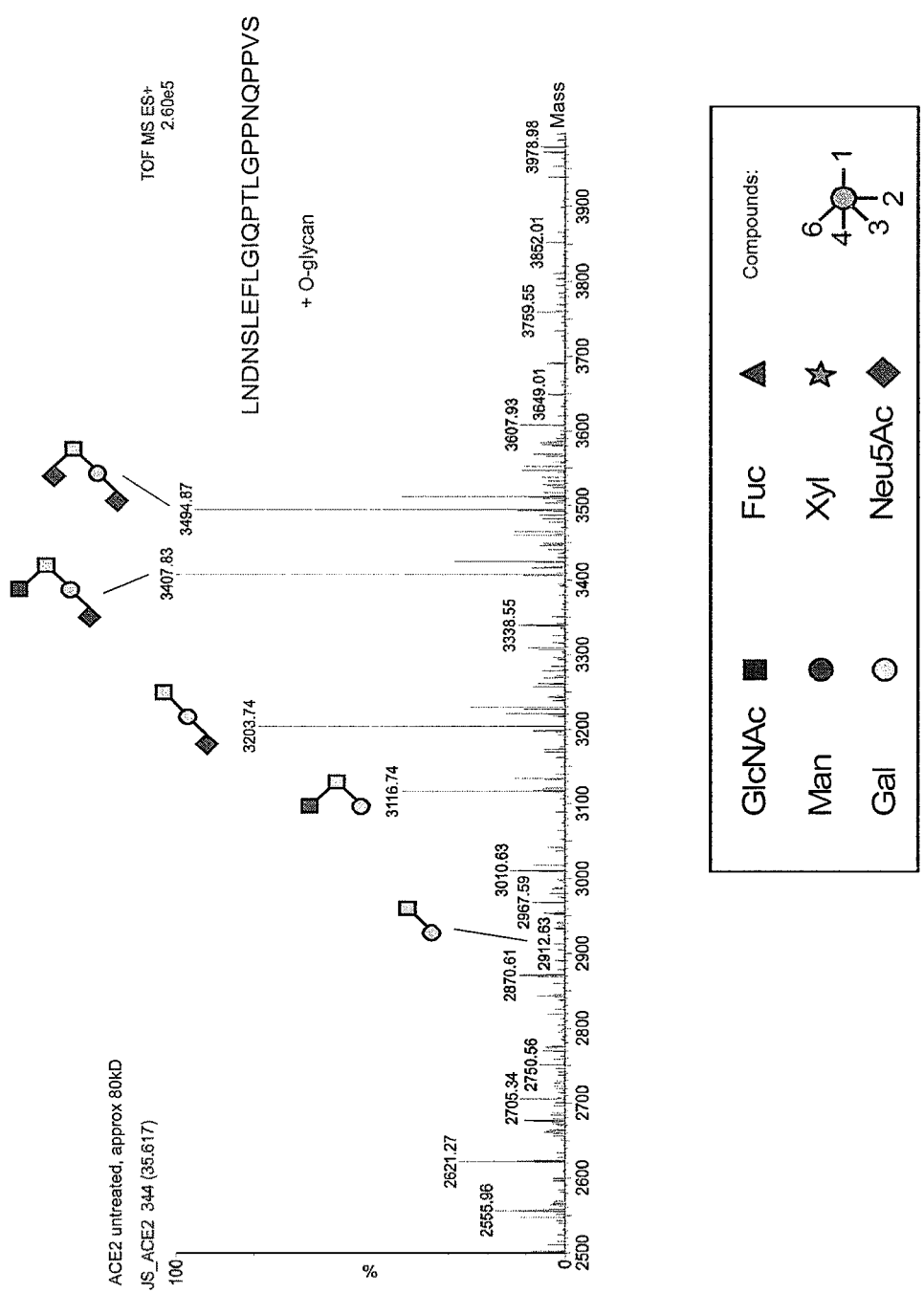
Figure 13:
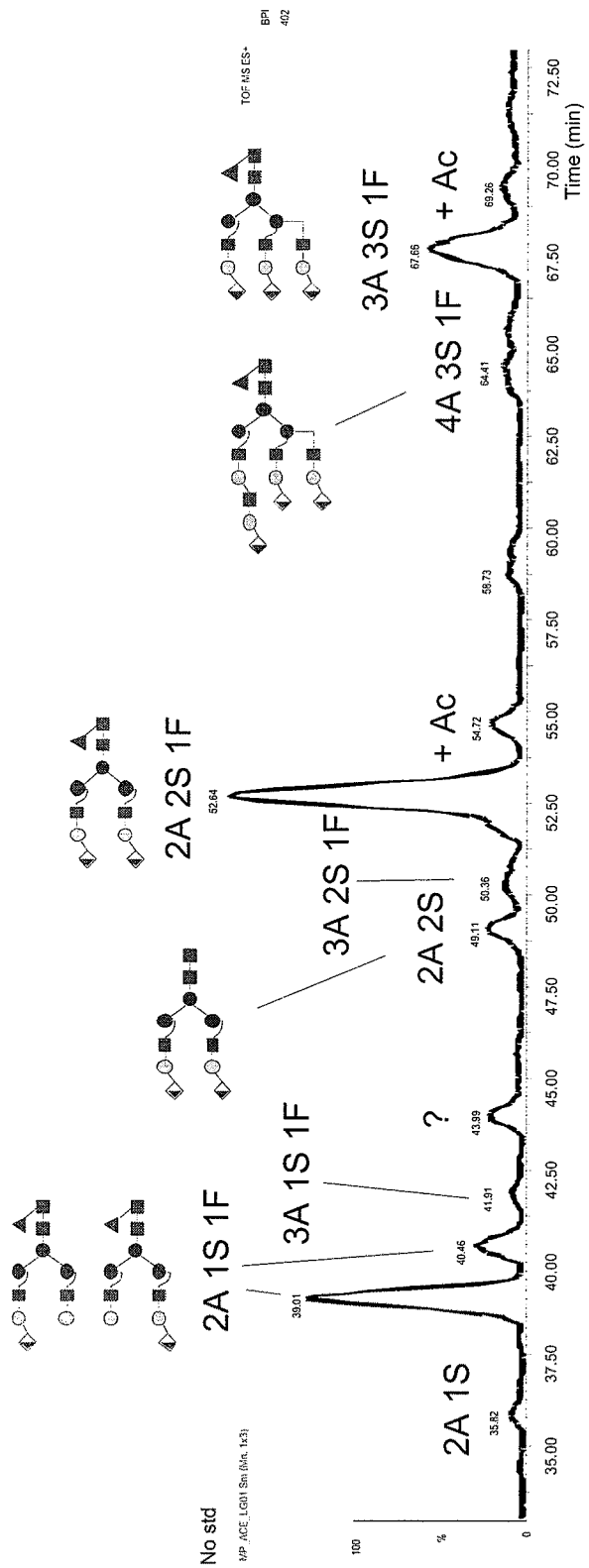
Figure 15:
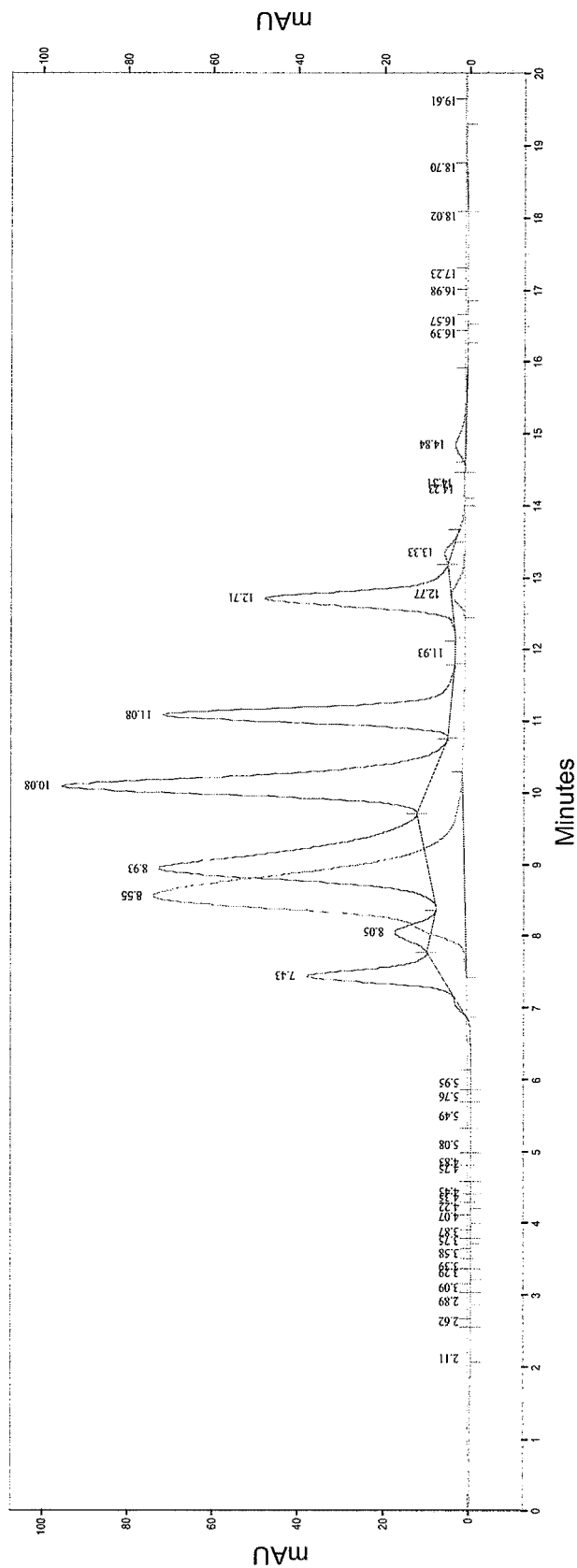
Figure 16:
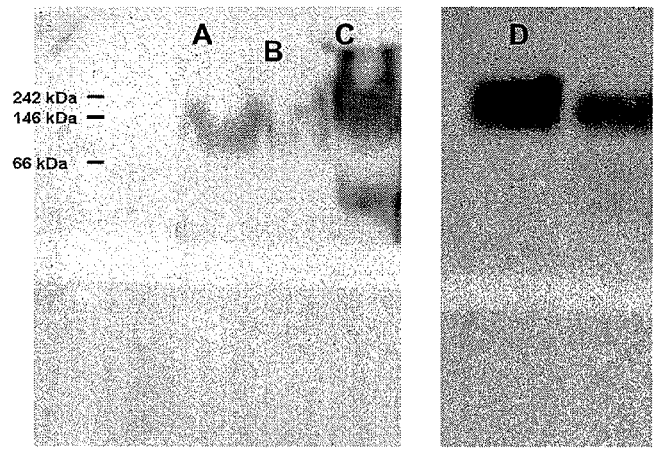
Figure 17:
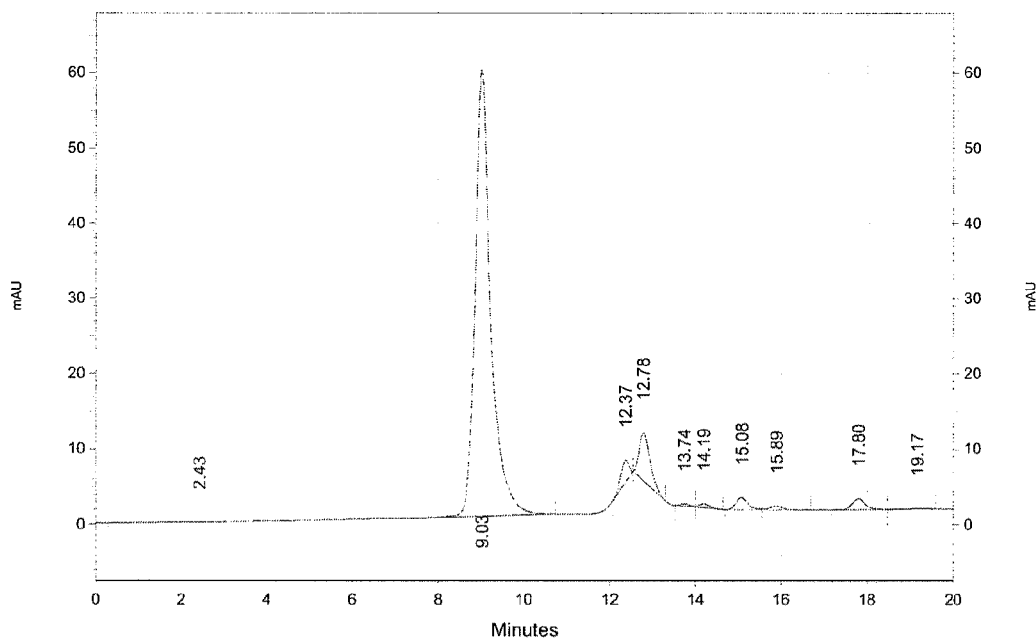
Figure 18:
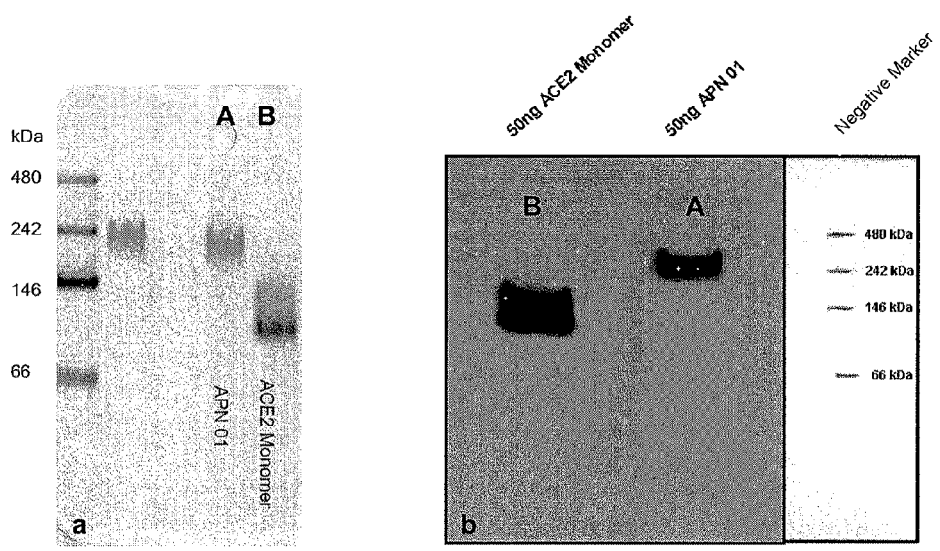
Figure 19:
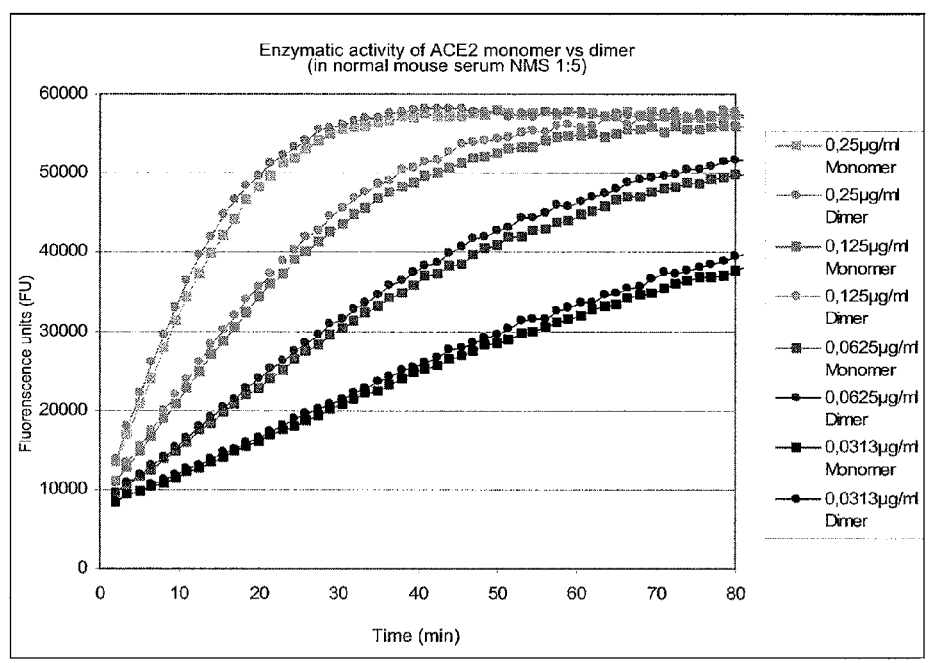
Figure 20:
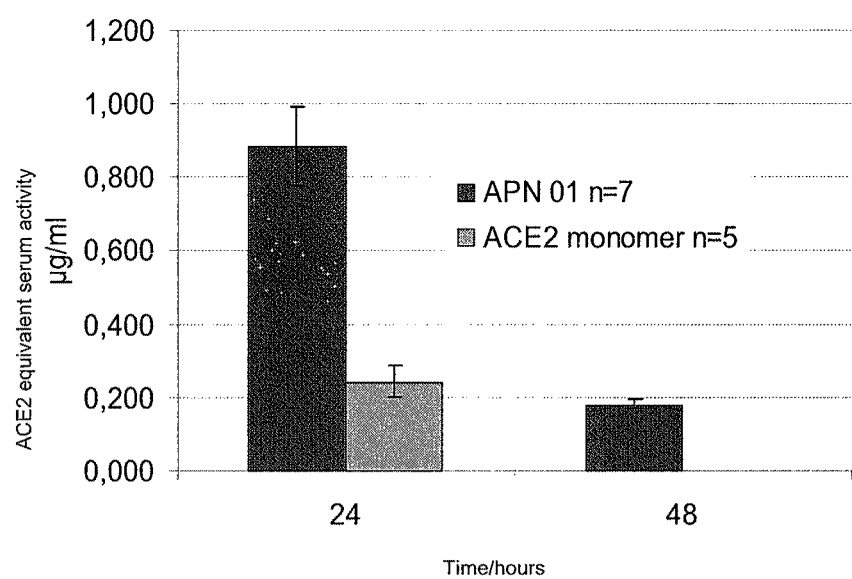

FIG. 1: ACE2 expression and selection cassette;
FIG. 2: ACE2-specific Western blot analysis of production clone history;
FIG. 3: SDS-PAGE analysis of ACE2 monomer;
FIG. 4: Clone selection;
FIG. 5: LC-MS glycosylaton analysis;
FIG. 6: Preparative size separation of ACE2;
FIG. 7: Pharmacokinetics of ACE2 in 3 species;
FIG. 8: Calibration curves for Ang 1-7 and Ang II quantification. The peptides were separated in the stated concentration range using RP-HPLC on Waters C18 µBondapak RP columns, 2.1×300 mm, 10 µm, 125 Å;
FIG. 9: MS/MS spectrum of N-terminal peptide. Note: Q and K have the same mass;
FIG. 10: Sequence of ACE2 and N-glycosylation prediction;
FIG. 11: Detailed spectrum for glycosylation site 103 (A), site 432 (B), site 546 (C), site 690 (D), site 90 (E);

FIG. 12: Spectrum of C-terminal O-glycosylated peptide. The structural assignment must be classified as provisional;

FIG. 13: LC-MS released glycans;

FIG. 14: Determination of ACE2 dimeric structure using native PAGE (left, protein bands visualized using silver stain) and SEC (right, separation on Zorbax G-450 column in presence of 220 mM Na-phosphate at pH 7.0 in 10% acetonitrile, the chromatogram was recorded at 214 nm);

FIG. 15: Chromatogram of size exclusion chromatography of the ACE2 dimer (retention time 8.55 min, 8.93 min). Standard: thyroglobulin (670 kDa, 7.43 min), gamma-globulin (158 kDa), ovalbumin (43 kDa, 10.08 min), myoglobulin (17 kDa, 11.08 min), vitamin B-12 (1.3 kDa, 12.71 min);

FIG. 16: ACE2-specific Western blot analysis of cell extracts from the cortex (A), brain (B) and a ACE2 dimer expression clone (C). D shows a pure ACE2 dimer;

FIG. 17: Analytical SEC-HPLC chromatogram of ACE2 monomer form. Run conditions: column: Zorbax GF250, buffer: 220 mM $Na_2H$—$PO_4$+10% $CH_3CN$, pH 8.0 at 1 mL/min;

FIG. 18: PAGE analysis of ACE2 dimers (A) and ACE2 monomers (B); proteins revealed using silver stain (a) and ACE2-specific Western blot (b);

FIG. 19: determination of enzymatic activity of ACE2 monomers in comparison with ACE2 dimers. A constant initial concentration of the fluorescence-labelled substrate cumarin-APK-DNP and four different enzyme concentrations were used and the corresponding fluorescence curves were compared;

FIG. 20: ACE2 serum activity measured 24 and 48 hours after ACE2 dimer administration (2.5 mg/kg, blue columns) or ACE2 monomeric form administration (2.5 mg/kg, grey columns).

EXAMPLES

Example 1

Expression of Highly Glycosylated ACE Dimer

The soluble fraction of the human ACE2 sequence (SEQ ID NO: 1) was cloned into an expression vector into which the amplified DHFR selection marker had already been added, to result in enhanced expression of the ACE2 gene. To this end, between the genes coding for ACE2 and dhfr, an attenuated IRES was inserted which allowed bi-cistronic transcription of ACE2 and DHFR onto the same mRNA. The ACE2 expression and selection cassette is shown graphically in FIG. 1. Since both proteins are expressed under the control of the same promoter, ACE2 expression can be intentionally enhanced by means of DHFR selection using the MTX antagonist. This strategy can produce particularly stable expression cell lines which provide high yields of a product with a constant quality. This also means that reasonable product titers can also be obtained in cell lines which may possibly be less suitable for recombinant expression of a specific target protein.

This vector was transfected in CHOdhfr cells and the copy number of the ACE2 gene was amplified under continuously increasing MTX pressure. Several selection and subcloning cycles were used to select the best products with optimized product properties using intracellular FACS analysis and protein-chemical as well as enzymatic analysis: in particular, to select the most suitable clones, the specific enzymatic activity, which was measured with 3 different substrates, the product homogeneity, the cellular productivity, and also the sugar complexity were taken into account. FIG. 2 shows a summary of Western blot analysis of the successive culture residues of individual clones which were used to establish the production cell line. The product properties of the individual clones differ in that the proportion of sugar in the expression product increases from right to left, as shown by the substantial increase in mass. This was obtained by specific selection of highly glycosylated clones. Finally, one clone (clone 5B9) which had the expression product with the highest molecular weight was used to establish the production cell line (184).

It was decided to pursue matters with 6 clones which enzymatically expressed highly active and complex N-glycosylated ACE2. While soluble ACE2 has a molecular weight of 83 kDa, clones were selected which were in the range of up to 120 kDa in denaturing SDS-PAGE, as determined by its sugar structure. FIG. 3 shows an ACE2 (lane B) produced by the present production process compared with a standard ACE2 produced in NS0 (lane A). While the ACE2 polypeptide in accordance with the invention—analyzed here as the monomer—is homogeneous and highly glycosylated and thus appears as a single band at approximately 120 kDa, the bands for the reference material are from 83 kDa to 120 kDa, indicating highly heterogeneous glycosylation.

The preliminary clones were then transferred onto protein-free growth medium (Polymun). This commercially available medium is chemically defined, serum-free, free of animal proteins and optimized for recombinant expression of glycoproteins in CHO. Fermentation was carried out with 2.5-3.5 µM $Zn^{2+}$. All 6 clones were kept under culture and tested for their production process suitability. In particular, the growth rates were recorded and the quantities of product and metabolites were examined (FIG. 4). Further, the expression products and the clones were precisely analyzed. All clones expressed highly active ACE2 and had productivities of 20-30 pg/cell/day. Further, the sugar structures and the heterogeneity thereof were analyzed. Finally, clone 1B4 was selected. Over the entire production process, it exhibited a homogeneous sugar structure. All 7 N-glycosylation sites were processed; they had at least a bi-, but occasionally even tri-branched complex glycosylation with terminal sialic acids.

A master cell bank was produced and tested based on this clone, and a GMP-class purification process and further on, a GMP-class production process were constructed.

SEQ ID NO: 1 (ACE2 protein sequence; the autologous signal sequence (underlined) is cleaved by the host cell for expulsion):

<u>MSSSSWLLLSLVAVTAA</u>

QSTIEEQAKTFLDKFNHEAEDLFYQSSLASWNYNTNITEENVQNMNNAGD

KWSAFLKEQSTLAQMYPLQEIQNLTVKLQLQALQQNGSSVLSEDKSKRLN

TILNTMSTIYSTGKVCNPDNPQECLLLEPGLNEIMANSLDYNERLWAWES

WRSEVGKQLRPLYEEYVVLKNEMARANHYEDYGDYWRGDYEVNGVDGYDY

SRGQLIEDVEHTFEEIKPLYEHLHAYVRAKLMNAYPSYISPIGCLPAHLL

GDMWGRFWTNLYSLTVPFGQKPNIDVTDAMVDQAWDAQRIFKEAEKFFVS

VGLPNMTQGFWENSMLTDPGNVQKAVCHPTAWDLGKGDFRILMCTKVTMD

DFLTAHHEMGHIQYDMAYAAQPFLLRNGANEGFHEAVGEIMSLSAATPKH

LKSIGLLSPDFQEDNETEINFLLKQALTIVGTLPFTYMLEKWRWMVFKGE

IPKDQWMKKWWEMKREIVGVVEPVPHDETYCDPASLFHVSNDYSFIRYYT

RTLYQFQFQEALCQAAKHEGPLHKCDISNSTEAGQKLFNMLRLGKSEPWT

-continued

LALENVVGAKNMNVRPLLNYFEPLFTWLKDQNKNSFVGWSTDWSPYADQS

IKVRISLKSALGDKAYEWNDNEMYLFRSSVAYAMRQYFLKVKNQMILFGE

EDVRVANLKPRISFNFFVTAPKNVSDIIPRTEVEKAIRMSRSRINDAFRL

NDNSLEFLGIQPTLGPPNQPPVS

Dimerization of ACE2 directs all of the hydrophobic protein units into the interior of the complex, whereupon the charged residues, such as N-bound sugar chains, project outwardly and solvate the structure in the charged physiological medium. Said dimerization by expression of a completely N-glycosylated ACE2 was observed in the presence of $Zn^{2+}$. In this case, the dimer complex consisted of 2 identical subunits, which were electrostatically bound to each other and also no longer separated in physiological solutions. This leads to the secretion of a glycoprotein each time with 14 highly charged sialic acid structures on each ACE2 molecule as well as 28 sialic acid structures in the dimer. Two $Zn^{2+}$ ions are each time inserted in the complex and stabilize its structure. The high charge of the sugar chains solvate the molecule in aqueous physiological solutions and force the associated charged protein domains outwards. The production process is constructed so that only ACE2 dimers are present in the end product.

This is rendered possible by dint of the fact that on generating the ACE2, sufficient $Zn^{2+}$ ions are present (preferably 1.5-5 micromolar $Zn^{2+}$ is used; in particular, the fermentation can be carried out at 2.5-3.5 μM $Zn^{2+}$; the subsequent treatment steps are carried out in the presence of $Zn^{2+}$ ions.

Purification is carried out using an anion exchange step, an ammonium sulphate precipitation, a HIC step, a cation exchange step then a further high resolution anion exchange step. All of the media in the process were phosphate buffered and contained sodium chloride. The final sample buffer is a physiological glycine solution for injection.

Example 2

Product Properties

Complexed, highly glycosylated ACE2 monomer or monomer units of the dimer have a much higher molecular weight than that indicated by the amino acid sequence due to the covalently bound sugar structures. Thus, peptide mapping provides a molecular mass of 102 kDa, while that of non-glycosylated ACE2 is only 83 kDa. The proportion of sugar is correspondingly 23% and is essential to the product properties described below. Because of the strong hydration, the monomer unit appears in SDS-PAGE at 120 kDa (FIG. 3) with respect to the reference standard.

The natural, membrane-bound ACE2 is not expressed, but only the soluble fraction of ACE2. Because of the missing membrane domain, it is completely glycosylated.

Because of the complex, highly sialyzed and thus highly negatively charged sugar structures, ACE2 has a much greater solubility compared with non-glycosylated or incompletely glycosylated ACE2. Thus, physiological buffered protein formulations of up to 15 mg/mL can readily be produced.

Further, the product is stable in solution and when stored longterm, it loses neither activity nor does it tend to degrade or aggregate, apart from stable dimerization. De-glycosylated ACE2, on the other hand, precipitates out even in low concentration ranges. This can be shown in a preparative deglycosylation experiment using PNGaseF. The theoretical stability index calculated for ACE2 is 41.2 and classifies the protein as unstable; the sugar structures are not considered for this calculation. However, since the formulations remain stable for months, this is clearly due to the high proportion of sugar. The better solvation of ACE2 also means that this formulation exclusively consists of ACE2 dimers (or after artificial separation to the monomer, exclusively of monomers), while non-glycosylated ACE2 tends to form multimers and aggregate.

Because the large fraction of charged sugar residues increases the hydrodynamic diameter, the solvation sheath of the present ACE2 preparation increases substantially. This situation can be exploited for the preparative purification of ACE2 by size separation columns; here, the protein which is exclusively present as a dimer has an apparent molecular weight of 250 kDa compared with the calculated 83 kDa. A chromatogram of a preparative ACE2 purification is shown in FIG. 6. ACE2 (first drawing) elutes with a retention time of 69 minutes. This corresponds to an apparent molecular weight between that of thyroglobulin (first drawing, 58 minutes, 670 kDa) and gamma-globulin (first drawing, 74 minutes, 158 kDa). In this high molecular weight region, there is practically no contamination in the culture residues, and so very pure product can be separated in a very simple separation step.

Example 3

Pharmacological Product Properties

The ACE2 preparation of the invention is present in physiological buffers as a stable, very pure and concentrated protein solution and can be stored and can be administered without further stabilization. A phosphate buffer may, for example, be employed.

ACE2 is stable as the monomer or dimer in solution and because of the high proportion of sugar, it exhibits no aggregation.

Further, the ACE2 preparation has full enzymatic activity.

Because of its solubility, ACE2 can be administered i.v. as a bolus. For the same reasons the bioavailability is guaranteed immediately after administration.

Because of the high, highly branched and complex proportion of sugar, ACE2 is degraded only slowly. This results in a long half time of at least 10.5 hours, which has been measured in various species, in particular in rhesus macaques. FIG. 7 shows the half times measured for ACE2 administered i.v. in 3 species.

The high sialic acid content also means that no neutralizing immune response is mounted against ACE2. This would not only be counter-productive for the exogenous administration of ACE2, but also could neutralize autologous ACE2 present in cells.

The ACE2 formulation described along with all of the associated product properties thus provide an effective therapy with rhA-CE2.

Example 4

Determination of Specific ACE2 Activity

The specific activity of ACE2 preparations was determined by measuring the conversion of Ang II (Asp-Arg-Val-Tyr-11e-His-Pro-Phe). All measurements were carried out in triplicate in 100 μL aliquots. The enzymatic reaction was started by adding 250 ng/mL ACE2 to a 80 μM Ang II solution in 50 mM MES, 300 mM NaCl, 10 μM $ZnCl_2$ and 0.01% Brij-30 at a pH of 6.5. The samples were carefully mixed and incubated at 37° C. for exactly 18 minutes. The enzymatic reaction was stopped by adding 100 mM EDTA. For the analysis, the solutions were separated using RP-HPLC (Waters C18 µBondapak, 2.1 (300 mm, 10 µm, 125 Å) using a linear gradient of 10% to 60% $CH_3CN$ in 0.08% $H_3PO_4$ for 20 minutes at a flow rate of 1 mL/min. Further, both Ang II and Ang 1-7 peaks were detected in the chromatogram and integrated. The peptide concentrations were determined using the appropriate calibration curves shown in FIG. 8. Further, the enzymatic conversion and the specific enzyme activity were determined.

The activity of the ACE2 product was determined as described above. Table 1 shows the results of peak integration as well as the computed enzyme data.

TABLE 1

Enzyme data and reaction conditions. The mean value of triplicated determinations is shown.
Enzymatic reactivity

| Peak surface area mAU · min | Conversion µmol · min$^{-1}$ | Reaction time min | ACE2 conc ng · mL$^{-1}$ | Ccat s$^{-1}$ | Specific activity µmol · mg$^{-1}$ · min$^{-1}$ |
|---|---|---|---|---|---|
| | | | Ang II | | |
| 17149890 | 62.1 | 18 | 250 | 8.0 ± 0.3 | 4.7 ± 0.2 |
| | | | Ang 1-7 | | |
| 4720141 | 23.1 | 18 | 250 | 8.8 ± 0.2 | 5.2 ± 0.1 |

The ACE2 preparation had a catalytic activity, ccat, of 8.0±0.3 s$^{-1}$ measured using the Ang II conversion, and 8.8±0.2 s$^{-1}$ with respect to the Ang 1-7 conversion. Both values were in good agreement and were much higher than the data given by Vickers et al (J Biol Chem 277, (17) (2002): 14838-43), which published a catalytic ACE2 activity of 3.5 s$^{-1}$. The reaction conditions were identical. The reason for the 240% higher activity for our preparation must be post-translational modifications and in this case primarily N-glycosylation, which was much less pronounced in the material used by Vickers. This material was expressed in insect cells and indeed had the same amino acid sequence, but was glycosylated to a much lesser extent and degree of branching. Furthermore, a commercially available ACE2 preparation from R&D Systems (cat no 933-ZN) which also had a much lower activity, ccat, of 2.0±0.1 s$^{-1}$, was examined. An essential property of the preparation of the invention is the particularly high enzymatic activity which was primarily permitted by post-translational modifications.

Example 5

Glycoproteomic Analysis of Recombinant ACE2

The sample of purified, CHO-expressed ACE2 was analyzed in two manners:

Firstly, tryptic peptides were produced using SDS-PAGE and S-alkylation and analyzed using LC-ESI-MS (and MS-MS). The N-terminal peptide and several internal peptides were found. Five of the seven potential N-glycosylated sites were found in the glycosylated form with glycan structures which mainly contained di-branched glycans with fucose and various quantities of sialic acid. The C-terminal peptide appeared to be O-glycosylated.

Secondly, free, reduced N-glycans were analyzed using carbon-LC-ESI-MS. For the di-branched, di-sialyzed glycan with fucose, it was shown that the fucose was bound to the α1,6 nucleus and the sialic acid was α2,3-bound. In addition to mono- or di-sialyzed, di-branched glycans, a considerable quantity of tri-branched oligosaccharide was found. A coarse estimate of the mass of the glycosylated ACE2 produced 101-102 kDa, i.e. consisting of approximately 17% carbohydrate.

Proteolytic Digestion of hBChE Separated Using SDS-PAGE.

Aliquots of ACE2 underwent SDS-PAGE, were destained, carbami-domethylated, digested with sequencing quality trypsin and extracted on gel pieces as described. The extracts were dried in a Speed Vac concentrator and re-constituted with water containing 0.1% formic acid before the subsequent LC-MS analysis. For the oligosaccharide analysis, the peptide was digested with PNGase F and the glycans were purified using C18 SPE cartridges.

MS Analysis of Tryptic Peptides and Glycol Peptides

The mass spectrometric analysis was carried out on a Q-TOF Ultima Global instrument (Waters Micromass) provided with a standard electrospray unit, a Cap-LC system (Waters Micromass) and a 10 port solvent exchange module (Rheodyne) as recently described [Kolarich 2006]. The samples were initially captured on an Aquasil C18 preliminary column (30×0.32 mm, Thermo Electron) using water as the solvent. The analytical column, a Biobasic C18 column (100×0.18 mm, Thermo Electron) was maintained prior to the solvent exchange on 5% acetonitrile and then a linear gradient of 5% to 50% acetonitrile was applied with a flow rate of 2 µL/min. All of the elution media contained 0.1% formic acid.

The samples were analyzed by MS- and also by MS-MS. The data analysis was carried out using MassLynx 4.0 SP4 software (Waters Micromass).

Analysis of Free N-Glycans from ACE2

Borohydride-reduced glycans were separated on a porous graphitic carbon column and assayed using mass spectrometry.

Example 6

Glycosylation Analysis

The molecular weight, the position of all the glycosylation sites as well as the structure of the bound sugar for the ACE2 protein sequence were determined herein. The sample was analyzed using tryptic digestion, S-alkylation and LC-ESI-MS.

The determined protein mass of the glycosylated product was 102 kDa, wherein the proportion of sugar was 23% of the total mass;

the N-terminal end and the presence of all of the internal peptides of the sequence were determined here (see sequence information);

all 7 postulated N-glycosylation sites (positions 53, 90, 103, 322, 432, 546 and 690) actually contained di-branched, complex sialic acid-containing fucosylated sugar structures (FIG. 13);

the C-terminal peptide was O-glycosylated.

The structure of these sugar residues was determined by carbon-LC-ESI-MS after cleavage and reduction. Each and all of the di-branched structures contained two α2,3-bound sialic acids and one α1,6-bound fucose. Small quantities of tri-branched structures were also found (FIG. 11). The selection strategy employed meant that a completely glycosylated and sialic acid-containing expression product was obtained.

Method:

Sample Preparation

ACE2 was separated using SDS-PAGE, destained, alkylated and digested using trypsin (Kolarich et al, Proteomics 6 (2006): 3369-3380). Gel extracts were dried and were dissolved in 0.1% formic acid prior to LC-MS analysis. For the sugar analysis, the peptide were digested with PNGase-F and purified on C18 SPE columns.

MS Analysis

All of the mass spectroscopic analyses were carried out using the Q-TOF Ultima Global instrument (Waters Micromass) with a standard electrospray unit and a Cap-LC system (Waters Micro-mass) (Kolarich, 2006).

The samples were concentrated on an Aquasil C18 preliminary column (30×0.32 mm, Thermo Electron) in water. The separation column used was a C18 column (100×0.18 mm, Thermo Electron) using an acetonitrile gradient. The samples were assayed in MS and MS-MS mode.

Analysis of Free N-Glycans

Glycans reduced using borohydride were characterized on a porous graphite column.

Example 7

Dimerization of rhACE2

ACE2 produced in accordance with Example 1 was obtained as the dimer and analyzed in this example as such without separating the dimers. Native treatment means that the dimer remained intact, in contrast to denaturing analysis (FIG. 3). The term "dimerization of ACE2" means all hydrophobic protein units are directed towards the interior of the complex, whereupon the charged residues, such as N-bound sugar chains, project outwardly and solvate the structure in the physiological medium which is also charged. This dimerization by expression of a completely N-glycosylated ACE2 was established in the presence of $Zn^{2+}$. The dimer complex in this case consists of two identical subunits which are bound together electrostatically and also do not separate any further in physiological solutions. This amounts to secretion of a glycoprotein each time with 14 highly charged sialic acid structures on each ACE2 molecule as well as 28 sialic acid structures in the dimer. Each has two $Zn^{2+}$ atoms inserted into the complex which stabilizes the structure. The high charge on the sugar chain solvates the molecule in aqueous physiological solutions and forces the associated charged protein domains outwards. The production process is constructed so that exclusively ACE2 dimers are present in the final product.

This is rendered possible by the fact that on generating rACE2s, sufficient $Zn^{2+}$ ions are present (preferably, 1.5-5 micromolar $Zn^{2+}$ is used; in particular, the fermentation can be carried out at 2.5-3.5 µM $Zn^{2+}$) and then the further treatment steps are carried out in the presence of $Zn^{2+}$ ions.

In FIGS. 14 and 15, dimerization of the ACE2 complex is determined using different methods. In native poly-acrylamide gel electrophoresis, following silver staining the protein was revealed as a single band with a size of approximately 250 kDa. Size separation chromatography on a Zorbax G-450 column in the presence of 10% acetonitrile in 220 mM Na-phosphate buffer at a pH of 7.0 also produced a single peak for the product at a retention time corresponding to a molecular weight of approximately 250 kDa. It should be noted that in both cases, exclusively dimerized protein was determined. Neither monomer structures nor high molecular weight aggregates were observed.

Example 8

ACE2 Dimers—Differences from Membrane-Bound ACE2

ACE2 is expressed as a transmembrane protein in all higher species, primarily in the kidney, heart, lung and liver cells, as an essential enzyme of the renin angiotensin system. Membrane-bound ACE2 surrounds itself in nature in the membrane lipid double layer with other membrane proteins which stabilize ACE2 in an active conformation and also protect the extracellular domains of ACE2 from proteolytic degradation. In order to enhance the pharmacological properties of soluble ACE2 and especially the activity and stability of the soluble protein, an expression and production strategy was selected which exclusively produced stable dimeric ACE2 structures. It is primarily the C-terminal domain of the protein and its post-translational modifications which are essentially responsible for the dimerization. In order to emphasize the particularities of the ACE2 dimeric structure, the structure of membrane-bound ACE2 was analyzed using native PAGE and ACE2-specific Western blot (FIG. 16). Tracks A and B show cell extracts (cortex and brain) and track C shows a cell extract of a production clone for ACE2 dimers, produced in accordance with Example 1. The membrane-bound product here has a much lower molecular weight compared with the expression product of Example 1 (C and D), although the first consists of only the extracellular portion. This indicates that membrane-bound ACE2 is present as the monomer. On the other hand, the expression product consists of dimers which provide the product with pharmacological advantages. In track D, the purified final product is analyzed. This has only a single band with a molecular weight of approximately 240 kDa.

Example 9

Improved Pharmacological Properties of ACE2 Dimers

APN 01 designates a physiological ACE2 protein formulation which consists exclusively of ACE2 dimeric structures. Two ACE2 monomers at a time in this case form non-covalently bound complexes. The molecular biological constructs, the expression cell line, the fermentation process, the purification and the buffer for storing and application are selected or designed so that the final product exclusively contains stable ACE2 dimers. The dimer neither aggregates to larger complexes nor does it dissociate under physiological conditions to monomers.

In FIG. 15 (analytical SEC-HPLC chromatogram: APN 01 compared with a size separation standard (Bio-RAD GF-standard, blue curve). Run conditions: column: Zorbax GF250, buffer: 220 mM $Na_2HPO_4$+10% $CH_3CN$, pH 8.0 at 1 mL/min). APN 01 eluted in the form of a single peak at 8.6 minutes, which retention time is between that of thyroglobulin (680 kDa, retention time 7.4 minutes) and bovine gamma globulin (158 kDa, retention time 8.9 minutes). The calculated molecular mass of this complex is approximately 214 kDa. This approximately corresponds to the expected molecular weight of two ACE2 units each of 102 kDa.

For the purposes of comparison, ACE2 monomers in CHO cells were produced as a reference material, which were also analyzed using SEC-HPLC. Its chromatogram is shown in FIG. 17. The monomer-is form elutes with a retention time of 9.0 minutes, which corresponds to a molecular weight of about 110 kDa. Both products were also compared using PAGE (see FIG. 18*a*). While APN 01 (A) had a protein band with a molecular weight of approximately 240 kDa, the monomeric form (B) appeared at approximately 100 kDa. ACE2-specific Western blot established the identity of both products, as can be seen in FIG. 18*b*.

Both products exhibited an identical specific enzyme activity, measured using an activity test employing a fluorescence labelled substrate. As can be seen in FIG. 19, the curves for the same enzyme concentration of the monomeric and dimeric forms overlie one another.

In order to compare the pharmacological properties of both products, both preparations were administered to B1-6 mice intraperitoneally as a bolus injection of 2.5 mg/kg and the ACE2 enzyme activity in serum samples was measured after 24 and 48 hours (see FIG. 20). The protein concentration was adjusted so that each animal received 100 µL of a physiological protein solution. Each time, 7 animals were treated with APN 01 (ACE2 dimer) and 5 animals with ACE2 monomer. While prior to ACE2 administration, no ACE2 activity could be measured in any of the serum samples, after administration, systemic ACE2 activity was measured in all cases. Just 24 hours after application, both groups were significantly different (t test, $p<0.001$): while animals which had been treated with the ACE2 dimer had an activity corresponding to an ACE2 concentration of 0.9 µg/mL, activity corresponding to a concentration of 0.2 µg/mL was found in only one animal in the group which received monomeric ACE2. After 48 hours, in the group which had received ACE2 homodimer, there was still 0.2 µg/mL of activity, while in the group which had received the monomer, no more systemic ACE2 activity could be detected. These data show that the dimeric ACE2 form has a very significant pharmacological advantage.

---

The invention claimed is:

1. A recombinant angiotensin converting enzyme 2 (ACE2) polypeptide dimer, wherein the ACE2 polypeptide dimer has angiotensin II converting activity, and each monomer of the ACE2 polypeptide dimer consists of amino acids 18-740 of SEQ ID NO: 1.

2. A recombinant, angiotensin converting enzyme 2 (ACE2) polypeptide dimer, wherein the ACE2 polypeptide dimer has angiotensin II converting activity, a serine corresponding to Ser740 of SEQ ID NO: 1 is O-glycosylated, and each monomer of the ACE2 polypeptide dimer consists of amino acids 18-740 of SEQ ID NO: 1.

3. A recombinant angiotensin converting enzyme 2 (ACE2) polypeptide dimer, wherein the ACE2 polypeptide dimer has angiotensin II converting activity, at least 70% of N-glycosylation sites have sialic acids, and each monomer of the ACE2 polypeptide dimer consists of amino acids 18-740 of SEQ ID NO: 1.

4. A recombinant, angiotensin converting enzyme 2 (ACE2) polypeptide dimer, wherein the ACE2 polypeptide dimer has angiotensin II converting activity, N-glycosylation sites of Asn53, Asn90, Asn103, Asn322, Asn432, Asn546, and Asn690 of SEQ ID NO: 1 are sialyzed, and each monomer of the ACE2 polypeptide dimer consists of amino acids 18-740 of SEQ ID NO: 1.

5. A recombinant angiotensin converting enzyme 2 (ACE2) polypeptide dimer, wherein the ACE2 polypeptide dimer has angiotensin II converting activity, one or more of Asn53, Asn90, Asn103, Asn322, Asn432, Asn546, and Asn690 of SEQ ID NO: 1 are N-glycosylated, and each monomer of the ACE2 polypeptide dimer consists of amino acids 18-740 of SEQ ID NO: 1.

6. A recombinant angiotensin converting enzyme 2 (ACE2) polypeptide dimer, wherein the ACE2 polypeptide dimer has angiotensin II converting activity, glycan at the one or more of Asn53, Asn90, Asn103, Asn322, Asn432, Asn546 and Asn690 of SEQ ID NO: 1 has the structure of formula 1, 2, 3, 4, 5, 6, 7 or 8:

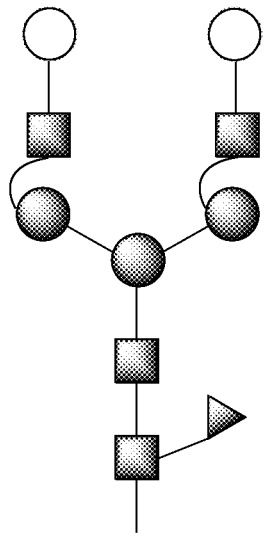

(formula 1)

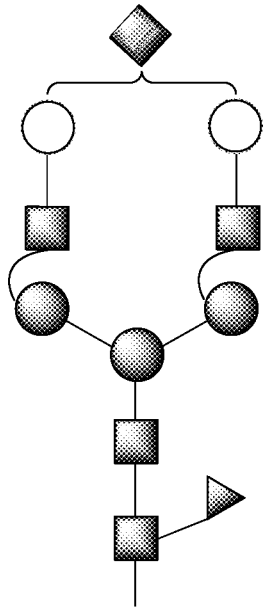

(formula 2)

(formula 3)
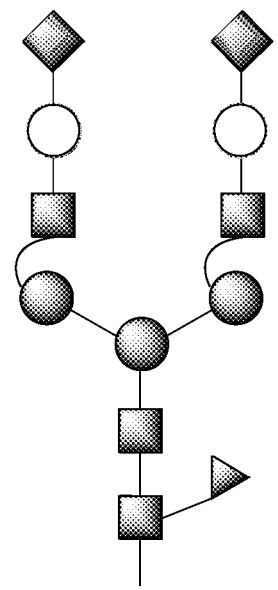
(formula 5)
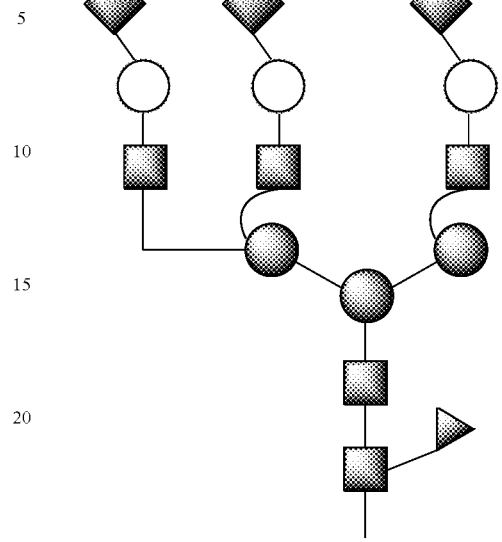
(formula 6)
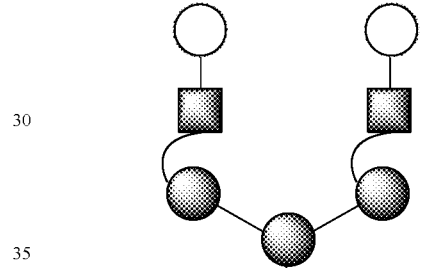
(formula 4)
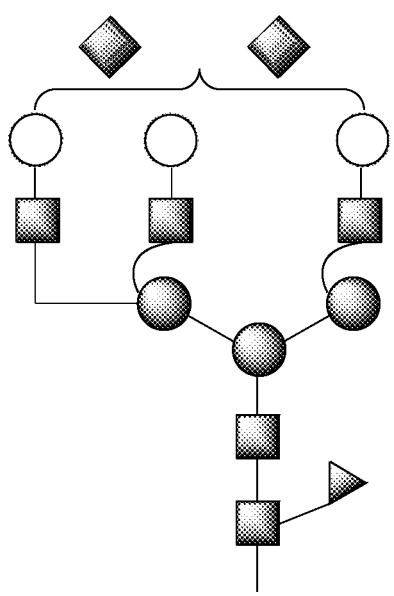
(formula 7)
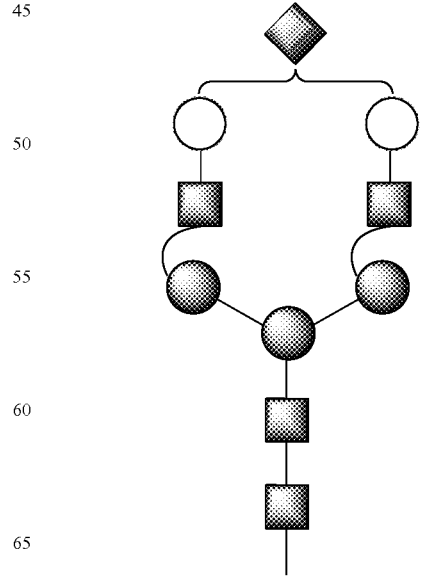

-continued (formula 8)

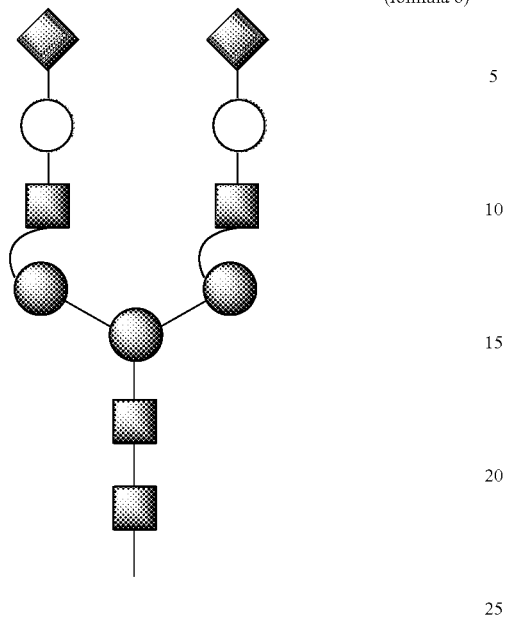

(formula 1)

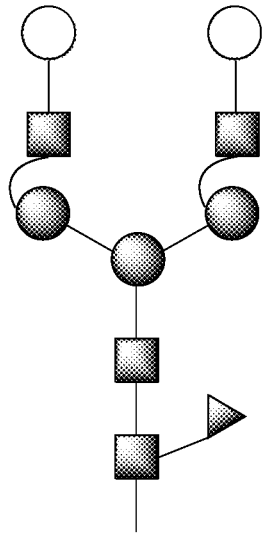

wherein

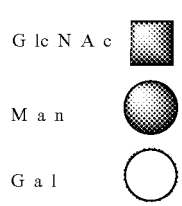

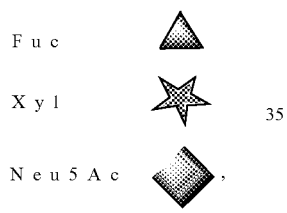

and each monomer of the ACE2 polypeptide dimer consists of amino acids 18-740 of SEQ ID NO: 1.

7. A composition comprising a recombinant angiotensin converting enzyme 2 (ACE2) polypeptide dimer, wherein the ACE2 polypeptide dimer has angiotensin II converting activity, at least 70% of the recombinant ACE2 polypeptides in the composition are present in the form of an ACE2 polypeptide dimer, and each monomer of the ACE2 polypeptide dimer consists of amino acids 18-740 of SEQ ID NO: 1.

8. The composition of claim 7, wherein less than 20% of the recombinant ACE2 polypeptides are present as ACE2 multimers.

9. A composition comprising a recombinant angiotensin converting enzyme 2 (ACE2) polypeptide dimer, wherein the ACE2 polypeptide dimer has angiotensin II converting activity; at least 70% of the recombinant ACE2 polypeptides in the composition are present in the form of an ACE2 polypeptide dimer, one or more glycosylation sites corresponding to Asn53, Asn90, Asn103, Asn322, Asn432, Asn546, and Asn690 of SEQ ID NO: 1 are N-glycosylated in more than 60% of the recombinant ACE2 polypeptides, and each monomer of the ACE2 polypeptide dimer consists of amino acids 18-740 of SEQ ID NO: 1.

10. The composition of claim 9, wherein the glycosylation sites are N-glycosylated with a glycan having the structure of formula 1, 2, 3, 4, 5, 6, 7 or 8:

(formula 2)

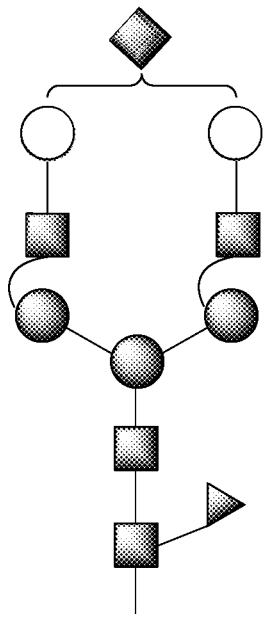

31
-continued
(formula 3)
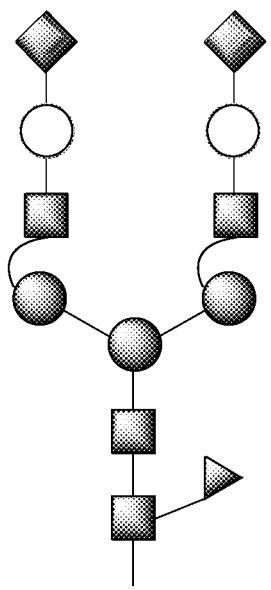
(formula 5)
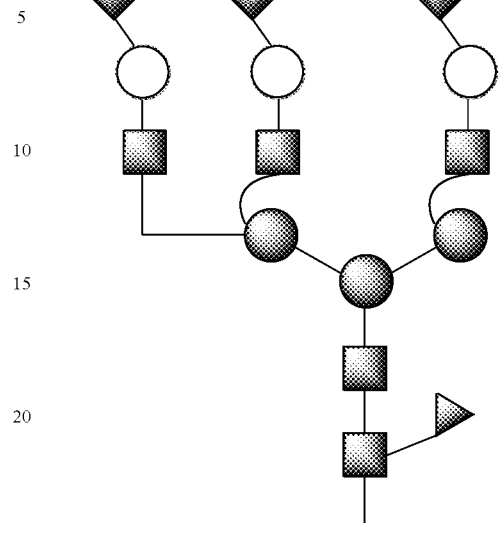
32
-continued
(formula 6)
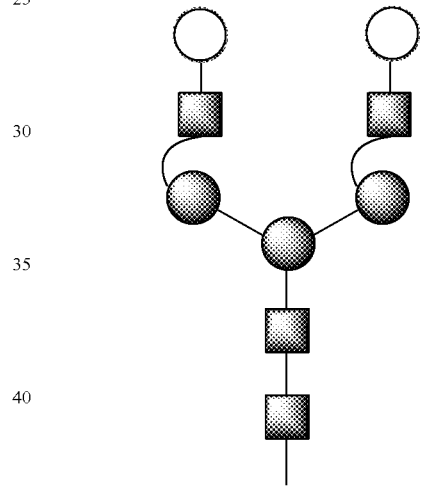
(formula 4)
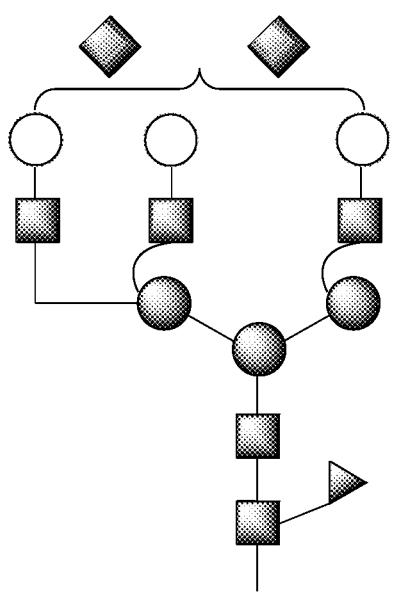
(formula 7)
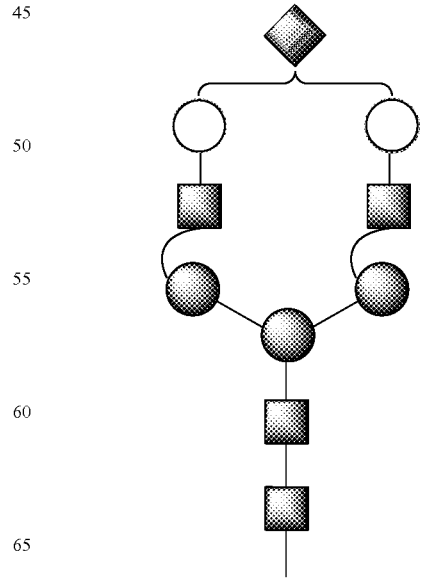

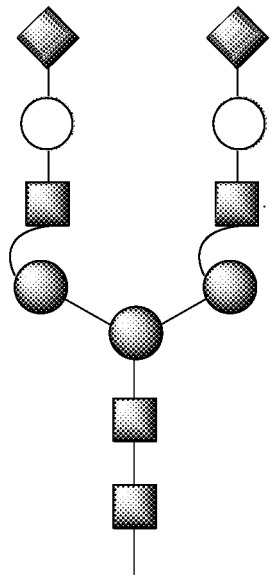
(formula 8)    in which:
GlcNAc  ▨        Fuc  △
Man  ●        Xyl  ★
Gal  ○        Neu5Ac  ◆
11. The composition of claim 9, wherein the glycosylation sites are N-glycosylated in more than 99% of the recombinant ACE2 polypeptides.
12. The composition of claim 7, further comprising a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 8,586,319 B2 | Page 1 of 1 |
| APPLICATION NO. | : 12/664641 | |
| DATED | : November 19, 2013 | |
| INVENTOR(S) | : Schuster et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this
Tenth Day of March, 2015

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 740
<212> TYPE: PRT
<213> ORGANISM: homo sapiens

<400> SEQUENCE: 1

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
```

-continued

```
                210                 215                 220
Asp Val Glu His Thr Phe Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
                275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
                435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Gln Ser Ile Lys Val Arg Ile Ser Leu
                610                 615                 620

Lys Ser Ala Leu Gly Asp Lys Ala Tyr Glu Trp Asn Asp Asn Glu Met
625                 630                 635                 640
```

```
Tyr Leu Phe Arg Ser Ser Val Ala Tyr Ala Met Arg Gln Tyr Phe Leu
                645             650                 655
Lys Val Lys Asn Gln Met Ile Leu Phe Gly Glu Glu Asp Val Arg Val
            660             665                 670
Ala Asn Leu Lys Pro Arg Ile Ser Phe Asn Phe Phe Val Thr Ala Pro
        675             680                 685
Lys Asn Val Ser Asp Ile Ile Pro Arg Thr Glu Val Glu Lys Ala Ile
    690             695                 700
Arg Met Ser Arg Ser Arg Ile Asn Asp Ala Phe Arg Leu Asn Asp Asn
705             710                 715                     720
Ser Leu Glu Phe Leu Gly Ile Gln Pro Thr Leu Gly Pro Pro Asn Gln
                725             730                 735
Pro Pro Val Ser
            740
```